US011638737B2

(12) United States Patent
Kim et al.

(10) Patent No.: US 11,638,737 B2
(45) Date of Patent: May 2, 2023

(54) **FOOD COMPOSITIONS AND PHARMACEUTICAL COMPOSITIONS CONTAINING *FILIPENDULA GLABERRIMA* EXTRACT FOR LOWERING BLOOD CHOLESTEROL LEVELS AND FOR AMELIORATING ATHEROSCLEROSIS**

(71) Applicant: KOREA INSTITUTE OF SCIENCE AND TECHNOLOGY, Seoul (KR)

(72) Inventors: Hyoung Ja Kim, Seoul (KR); Chang Bae Jin, Seoul (KR); Hyun Beom Lee, Seoul (KR); Hyun Soo Choi, Seoul (KR); You Bin Cho, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 5 days.

(21) Appl. No.: 17/023,447

(22) Filed: Sep. 17, 2020

(65) Prior Publication Data

US 2021/0106644 A1    Apr. 15, 2021

(30) Foreign Application Priority Data

Oct. 10, 2019  (KR) .................. 10-2019-0125191

(51) Int. Cl.
*A61K 36/73* (2006.01)
*A61K 9/00* (2006.01)
*C07H 15/24* (2006.01)

(52) U.S. Cl.
CPC ............ *A61K 36/73* (2013.01); *A61K 9/0019* (2013.01); *A61K 9/0056* (2013.01); *A61K 9/0095* (2013.01); *C07H 15/24* (2013.01); *A61K 2236/333* (2013.01)

(58) Field of Classification Search
CPC . A61K 36/73; A61K 2236/333; A23L 33/105; A23V 2200/326
See application file for complete search history.

(56) References Cited

U.S. PATENT DOCUMENTS

| 6,900,241 B2 * | 5/2005 | Romanczyk, Jr. ... A61K 9/2018 549/399 |
| 2012/0052138 A1* | 3/2012 | Park ............................... A61P 3/04 424/729 |

FOREIGN PATENT DOCUMENTS

| EP | 2780025 B1 | 12/2015 |
| EP | 3043809 B1 | 1/2018 |
| JP | 2003-183120 A | 7/2003 |
| KR | 10-2011-0122448 A | 11/2011 |
| KR | 10-2014-0045134 A | 4/2014 |
| KR | 10-1516764 B | 5/2015 |
| KR | 10-2016-0018051 A | 2/2016 |
| KR | 10-2016-0084990 A | 7/2016 |
| KR | 10-2017-0091306 A | 8/2017 |
| KR | 10-2018-0113013 A | 10/2018 |
| KR | 20210007686 A * | 1/2021 |

OTHER PUBLICATIONS

Yeo, Kor J Pharmacogn, 3, 23, 1992 (Year: 1992).*
Preventing Heart Disease, The Nutrition Source, Harvard T.H. Chan School of Public Health, 2022 (Year: 2022).*
Tabassum, Journal of Biochemical and Molecular Toxicology, 21, 3, 2007 (Year: 2007).*
Scott. M. Grundy, HMG-CoA Reductase Inhibitors for Treatment of Hypercholesterolemia, The New England Journal of Medicine, Jul. 7, 1988, pp. 24-33, vol. 319, No. 1.
Geraldine Mantell, Lipid Lowering Drugs in Atherosclerosis—the HMG-CoA Reductase Inhibitors, Clinical and Experimental Hypertension. Part A: Theory and Practice., 1989, pp. 927-941, vol. 11, No. 5-6.
Akiko Hamaoka et al., Effects of HMG-CoA reductase inhibitors on continuous post-inflammatory vascular remodeling late after Kawasaki disease, Journal of Cardiology, Aug. 1, 2010, pp. 245-253, vol. 56.
Ban Liu et al., Effect of Rosuvastatin on ROCK Activity, Endothelial Function, and Inflammation in Asian Patients with Atherosclerosis, Internal Medicine, Jan. 6, 2012, pp. 1177-1182, vol. 51, No. 10.
Alexey Y.Kolyada et al., 3-Hydroxy-3-Methylglutaryl Coenzyme A Reductase Inhibitors Upregulate Inducible NO Synthase Expression and Activity in Vascular Smooth Muscle Cells, Hypertension, 2001, pp. 1024-1029,vol. 38.
José Martinez-Gonzalez et al., HMG-CoA reductase inhibitors reduce vascular monocyte chemotactic protein-1 expression in early lesions from hypercholesterolemic swine independently of their effect on plasma cholesterol levels, Atherosclerosis, 2001, pp. 27-33, vol. 159.
Hideki Ito et al., A Comparison of Low Versus Standard Dose Pravastatin Therapy for the Prevention of Cardiovascular Events in the Elderly: The Pravastatin Anti-atherosclerosis Trial in the Elderly (PATE), Journal of Atherosclerosis and Thrombosis, Feb. 14, 2001, pp. 33-44, vol. 8, No. 2.
Esther Lutgens et al., HMG-coA reductase inhibitors: lipid-lowering and beyond, Drug Discovery Today: Therapeutic Strategies, 2004, pp. 189-194, vol. 1, No. 2.
Dalal Daham AL-Otaibi et al., Dyslipidemias and Role Of Statins In Their Therapy., Research Journal of Pharmaceutical, Biological and Chemical Sciences, 2015, pp. 449-460, vol. 6, No. I.
Yukichi Kishida et al.,Research and Development of Pravastatin, J Pharm Soc Japan, 1991, pp. 469-487,vol. 111, No. 9.

(Continued)

*Primary Examiner* — Robert A Wax
*Assistant Examiner* — William Craigo
(74) *Attorney, Agent, or Firm* — Goldilock Zone IP Law

(57) ABSTRACT

Disclosed are a *Filipendula glaberrima* alcoholic extract and solvent fractions fractionated therefrom or novel compounds 1 and 2 purely isolated from a *Filipendula glaberrima* ethyl acetate fraction that have an excellent inhibitory effect against HMG-CoA reductase activity, an excellent antioxidant effect and a remarkably excellent effect of suppressing the formation of foam cells in macrophages. Also, disclosed is a pharmaceutical composition or health food composition for treating, preventing and ameliorating vascular diseases, hypercholesterolemia, or heart diseases caused by hypercholesterolemia, or lowering blood cholesterol levels, containing, as active ingredients, the *Filipendula glaberrima* alcoholic extract and the solvent fractions or the novel compounds 1 and 2.

7 Claims, 12 Drawing Sheets

(56) References Cited

OTHER PUBLICATIONS

M. J.Tikkanen et al., Treatment of familial and non-familial hypercholesterolaemia: a rewiew of HMG-GoA reductase inhibitors and probucol, European Heart Journal, 8 Supplement E, 1987, pp. 97-101, Japan.

Hyun Ah Jung et al., Antioxidant Flavonoids and Chlorogenic Acid from the Leaves of Eriobotrya japonica, Arch Pharm Res, Nov. 5, 1999, pp. 213-218, vol. 22, No. 2, Korea.

Yoshiaki Miyake et al., Identification and Antioxidant Activity of Flavonoid Metabolites in Plasma and Urine of Eriocitrin-Treated Rats, J Agric Food Chem, 2000, pp. 3217-3224, vol. 48, No. 8, Japan.

J L Witztum et al., Role of oxidized low density lipoprotein in atherogenesis, The Journal of Clinical Investigation, Dec. 1991, pp. 1785-1792, vol. 88.

S Yla-Herttuala et al., Evidence for the presence of oxidatively modified low density lipoprotein in atherosclerotic lesions of rabbit and man, The Journal of Clinical Investigation, Oct. 1989, pp. 1086-1095, vol. 84, No. 4.

Jan.Galle et al., Impact of oxidized low density lipoprotein on vascular cells, Atherosclerosis, Nov. 8, 2005, pp. 219-226. vol. 185.

Marion M. Bradford, A Rapid and Sensitive Method for the Quantitation of Microgram Quantities of Protein Utilizing the Principle of Protein-Dye Binding, Analytical Biochemistry, Jan. 29, 1976, pp. 248-254, vol. 72.

M. J. Sanz et al., Influence of a series of natural flavonoids on free radical generating systems and oxidative stress, Xenobiotica, 1994, pp. 689-699, vol. 24, No. 7.

"Studies on Flavonoids of Filipendula purpurea Maxim", Qu Xiaoyu, China Excellent Master's Degree Thesis Full-text Database (Electronic Journal), Issue 09 Year: 2010.

"Study on Active Components of Inhibiting HMG-COA Reductase in Hawthorn and their Safety Evaluation", Huang Wenwen, China Journal of Chinese Materia Medica, vol. 35, Issue 18, pp. 2428-2431 Year: 2010.

"Research Development of Pharmacology Activities of Quercitrin", Yang Lin, Asia-Pacific Traditional Medicine, vol. 11, Issue 6, pp. 61-63 Year: 2010.

"Effect of Quercetin on ox-LDL-induced Lipid Accumulation and Peroxidation in Mouse Macrophages", Miao Cheng et al., Chinese Journal of Pathophysiology, vol. 29, Issue 8, pp. 1370-1374 Year: 2013.

"Quick View for What to Eat for Lowering Blood Pressure and Blood Fat", Wang Zhongliang, p. 163, Beijing: China Light Industry Press, 1st Edition, Mar. 2013.

"Health Preservation Book of Vegetable and Fruit Juice", Zhang Xuewei, p. 51, Beijing: Traditional Chinese Medicine Ancient Books Press, 1st Edition, Jul. 2015.

"Study on Extraction, Isolation and Activity of Chemical Components from Plant Stem and Leaf", Wei Qiang, pp. 67-68, Hefei: Anhui University Press, 1st Edition, Sep. 2018.

Communication from Chinese Patent Office dated Dec. 27, 2022, corresponding Chinese Patent Application No. 202011074636.2.

* cited by examiner

FOOD COMPOSITIONS AND PHARMACEUTICAL COMPOSITIONS CONTAINING *FILIPENDULA GLABERRIMA* EXTRACT FOR LOWERING BLOOD CHOLESTEROL LEVELS AND FOR AMELIORATING ATHEROSCLEROSIS

CROSS-REFERENCE TO RELATED APPLICATION

This application claims under 35 U.S.C. § 119(a) the benefit of priority to Korean Patent Application No. 10-2019-0125191 filed on Oct. 10, 2019, the entire contents of which are incorporated herein by reference.

BACKGROUND

(a) Technical Field

The present invention relates to a method for preparing a food composition and a therapeutic pharmaceutical composition containing an extract of *Filipendula glaberrima* for lowering blood cholesterol levels and for ameliorating atherosclerosis.

(b) Background Art

Cholesterol is present in every part of humans including the brain, nerves, muscles, skin, liver, intestines, heart and the like, and is an essential substance involved in various biochemical reactions as a component of the cell membrane in the body. However, excess cholesterol may be accumulated in vascular endothelial cells or the endothelium, causing vascular diseases such as hyperlipidemia and thus secondary diseases such as arteriosclerosis, hypertension, obesity, and diabetes. 3-Hydroxy-3-methylglutaryl-CoA reductase (hereinafter referred to as "HMG-CoA reductase") is an enzyme that mediates the synthesis of mevalonic acid, which is an intermediate in the biosynthetic pathway of sterol or isoprenoid compounds. When the activity of HMG-CoA reductase is lowered, an effect of lowering levels of lipid and cholesterol in the blood can be obtained through inhibition of the biosynthesis of cholesterol. Hyperlipidemia, especially hypercholesterolemia, causes arterial thrombosis due to abnormally distributed lipid deposition in arteries, including coronary arteries, carotid arteries and peripheral arteries, resulting in arteriosclerosis, in which lipids accumulate thickly along blood vessels, which reduces blood flow and thus causes ischemic heart diseases and/or cardiovascular disorders or diseases such as angina pectoris and myocardial infarction. As such, since hyperlipidemia and arteriosclerosis are closely related to each other, HMG-CoA reductase inhibitors can prevent arteriosclerosis by treating hyperlipidemia. Non-Patent Document 1 discloses that HMG-CoA reductase inhibitors are useful for the treatment of hyperlipidemia due to effects of lowering total cholesterol and LDL (low density lipoprotein)-cholesterol levels thereof. Non-Patent Documents 2 to 4 disclose that HMG-CoA reductase inhibitors are useful for the prevention and treatment of atherosclerosis. Non-Patent Documents 5 to 7 disclose that HMG-CoA reductase inhibitors are useful for the prevention and treatment of disorders or diseases associated with the cardiovascular system. Non-Patent Documents 8 to 12 disclose that HMG-CoA reductase inhibitors are useful for the prevention and treatment of atherosclerosis.

Meanwhile, Non-patent documents 13 to 14 disclose that reactive oxygen species (ROS) are known to produce peroxides and free radicals, etc., thus causing damage to cells, including proteins, fats, DNA and RNA, and to be involved in diseases such as arteriosclerosis, Parkinson's disease and Alzheimer's disease due to oxidation and lipid peroxidation of LDL. According to Non-patent documents 15 to 17, it is known that oxidized LDL is introduced into macrophages, endothelial cells, and smooth muscle cells, causing atherosclerosis, and at the stage of atherosclerosis, macrophages form foam cells due to the introduction of oxidized LDL, thereby causing atherosclerotic plaques. Atherosclerosis is a systemic vascular disease, and is the most common cause of thrombotic cerebral infarction, and is also the most common cause of myocardial infarction and peripheral vascular obstruction, as well as cerebral infarction. Currently, many drugs have been developed as HMG-CoA reductase inhibitors, and representative among these, statin drugs are widely used. Specific example of statin drugs includes lovastatin, simvastatin, rosuvastatin, pravastatin, fluvastatin, mevastatin, atorvastatin, cerivastatin and the like. However, statin drugs are known to cause side effects, etc. in the central nervous system.

Therefore, there is an urgent need to develop novel HMG-CoA reductase inhibitors free of side effects, or novel therapeutic and prophylactic agents for atherosclerotic vascular diseases capable of suppressing the formation of foam cells. Recently, there is increasing interest in natural pharmaceuticals to overcome the disadvantages (resistance, side effects, etc.) of synthetic pharmaceuticals or replace the same.

The above information disclosed in this Background section is only for enhancement of understanding of the background of the invention, and therefore it may contain information that does not form the prior art that is already known in this country to a person of ordinary skill in the art.

PRIOR ART DOCUMENT

Patent Document (Patent Document 1) Korean Patent Laid-open Publication No. 10-2014-0045134 entitled "Pharmaceutical composition for the prevention or treatment of obesity or metabolic diseases containing an extract of *Aster glehni* or a fraction thereof as an active ingredient"

(Patent Document 2) Korean Patent Laid-open Publication No. 10-2018-0113013 entitled "Pharmaceutical composition for prevention and treatment of arteriosclerosis, containing an extract of *Gracilariopsis chorda* or a fraction thereof as an active ingredient"

(Patent Document 3) Korean Patent Laid-open Publication No. 10-2016-0084990 entitled "Composition for the treatment of arteriosclerosis containing *Robinia pseudoacacia* L."

(Patent Document 4) Korean Patent Laid-open Publication No. 10-2016-001805 entitled "Anti-hyperlipidemic and anti-atherosclerotic composition containing a fermented *Panax* ginseng extract"

(Patent Document 5) Korean Patent Registration No. 10-1516764 entitled "A composition for the prevention or treatment of arteriosclerosis, containing an extract of *Humulus japonicus*"

Non-Patent Documents (Non-Patent Document 1) Grundy S. M., N. Engl. J. Med., 319(1): 24-33, 1988

(Non-Patent Document 2) Mantell G., Clin. Exper. Hyper. Part A, Theory and practice, 11(5-6), 927-41, 1989

(Non-Patent Document 3) Hamaoka A., et al., J. Cardiol. 56(2), 245-253, 2010

(Non-Patent Document 4) Liu B., et al., Int. Med. (Tokyo, Japan) 51(10), 1177-1182, 2012

(Non-Patent Document 5) Kolyada A. Y., et al., Hypertension, 38(5), 1024-1029, 2001

(Non-Patent Document 6) Martinez-Gonzalez J., et al., Atherosclerosis 159, 27-33, 2001

(Non-Patent Document 7) Ito H., et al., J. Atheroscler. Thromb. 8(2), 33-44, 2001

(Non-Patent Document 8) Lutgens E. and Daemen Mat J. A. P., Drug Discovery Today: Therapeutic Strategies 1(2), 189-194, 2004

(Non-Patent Document 9) AL-Otaibi D. D., and Novotny L., Res. J. Pharm. Biol. Chem. Sci., 6(1), 449-460, 2015

(Non-Patent Document 10) Kishida Y., et al., J. Pharm. Soc. Japan, 111(9), 469-487, 1991

(Non-Patent Document 11) Tikkanen M. J., et al., Euro. Heart J., 8 Suppl. E, 97-101, 1987

(Non-Patent Document 12) Jung H. A., et al., Arch. Pharm. Res., 22, 213-218, 1999.

(Non-Patent Document 13) Miyake Y., et al., J. Agric. Food Chem., 48, 3217-3224, 2000.

(Non-Patent Document 14) Witztum J. L., S. D., J. Clin. Invest., 88, 1785-1792, 1991.

(Non-Patent Document 15) Ylaherttuala S., et al., J. Clin. Invest., 84, 1086-1095, 1989.

(Non-Patent Document 16) Galle J., et al., Atherosclerosis 185, 219-226, 2006.

SUMMARY OF THE DISCLOSURE

The present invention has been made in an effort to solve the above-described problems associated with the prior art and, while investigating the pharmaceutical activity of natural raw materials, the present inventors found that an alcoholic extract of *Filipendula glaberrima*, solvent fractions fractionated therefrom, and novel compounds 1 and 2 exhibited excellent effects of inhibiting the activity of HMG-CoA reductase and of suppressing the formation of foam cells, which are formed due to the introduction of oxidized LDL in macrophages, and further exhibited an excellent antioxidant effect. Based on this finding, the present invention has been completed.

Thus, it is one object of the present invention to provide a pharmaceutical composition having an inhibitory effect against HMG-CoA reductase activity, an antioxidant effect and an effect of suppressing the formation of foam cells for treating, ameliorating and preventing hypercholesterolemia, or heart diseases or vascular diseases caused by hypercholesterolemia, the pharmaceutical composition containing, as active ingredients, an alcoholic extract of *Filipendula glaberrima* or a fraction thereof and novel compounds 1 and 2.

It is another object of the present invention to provide a health food composition having an inhibitory effect against HMG-CoA reductase activity, an antioxidant effect and an effect of suppressing the formation of foam cells for treating, ameliorating and preventing hypercholesterolemia, or heart diseases or vascular diseases caused by hypercholesterolemia, the pharmaceutical composition containing, as active ingredients, an alcoholic extract of *Filipendula glaberrima* or a fraction thereof and novel compounds 1 and 2.

It is another object of the present invention to provide a method for preparing an alcoholic extract of *Filipendula glaberrima* or a solvent fraction thereof fractionated therefrom, and a method for preparing novel compounds 1 and 2 having an excellent inhibitory effect against HMG-CoA reductase activity from an ethyl acetate fraction fractionated therefrom through a series of isolation steps using column chromatography, etc.

It is another object of the present invention to provide a pharmaceutical composition having an antioxidant effect for treating and preventing heart diseases or vascular diseases, the pharmaceutical composition containing, as an active ingredient, an alcoholic extract of *Filipendula glaberrima* or a solvent fraction fractionated therefrom.

The objects of the present invention are not limited to those described above. The objects of the present invention will be clearly understood from the following description and can be implemented by the means defined in the claims and combinations thereof.

In order to accomplish the objects described above, the present invention provides the following composition or compound:

In one aspect, the present invention provides a composition containing, as active ingredients, a *Filipendula glaberrima* alcoholic extract or a fraction thereof and a novel compound represented by the following Formula 1 or 2:

[Formula 1]

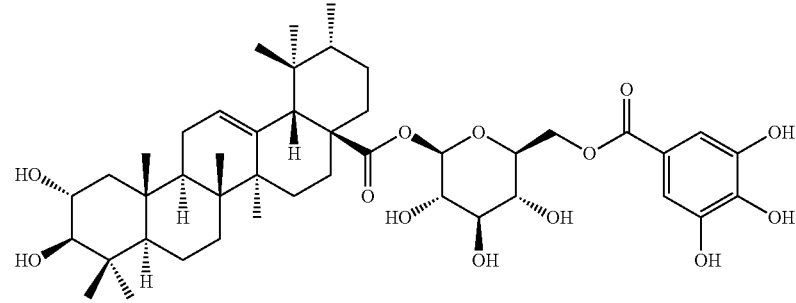

-continued

[Formula 2]

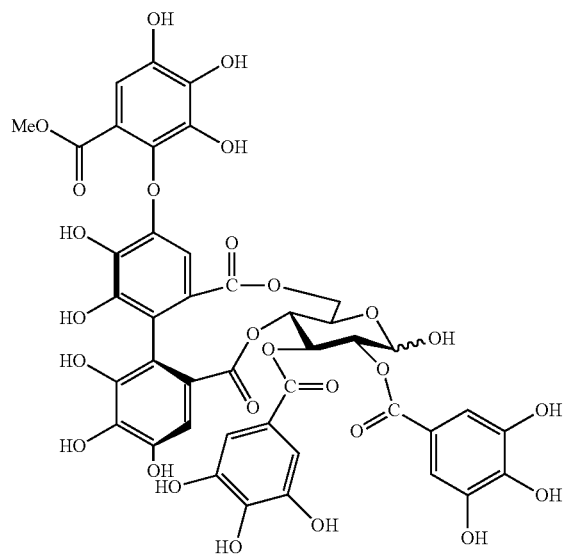

The composition may be a pharmaceutical composition or a health food composition for treating, ameliorating and preventing hypercholesterolemia, or heart diseases or vascular diseases caused by hypercholesterolemia.

In another aspect, the present invention provides a method for isolating active compounds from a solvent extract of *Filipendula glaberrima* having excellent activities of lowering blood cholesterol levels and ameliorating hyperlipidemia or an ethyl acetate fraction of the extract, the method including the following steps:

(Step 1) a first step of obtaining a solvent fraction by preparing a $C_1$-$C_5$ alcohol extract of *Filipendula glaberrima* and fractionating the extract with dichloromethane, ethyl acetate or butanol; and (Step 2) a second step of obtaining novel compounds 1 and 2 using $C_1$-$C_5$ alcohol and an organic solvent from the ethyl acetate fraction obtained in the first step by a series of isolation steps using silica gel, Sephadex LH-20, Toyopearl HW-40, reverse-phase silica gel, HPLC, etc.

In another aspect, the present invention provides a composition containing, as active ingredients, the alcoholic extract of *Filipendula glaberrima* and the solvent fraction fractionated therefrom, or the novel compound represented by Formula 1 or 2 purely isolated from an ethyl acetate fraction of *Filipendula glaberrima* fractionated therefrom, obtained in the first and second steps above.

The composition may be a pharmaceutical composition or a health food composition for treating and preventing hypercholesterolemia or heart diseases or vascular diseases caused by hypercholesterolemia.

Other aspects and preferred embodiments of the invention are discussed infra.

BRIEF DESCRIPTION OF THE DRAWINGS

The above and other features of the present invention will now be described in detail with reference to certain exemplary embodiments thereof, illustrated in the accompanying drawings which are given herein below by way of illustration only, and thus are not limitative of the present invention, and wherein.

DETAILED DESCRIPTION

Figure 1:
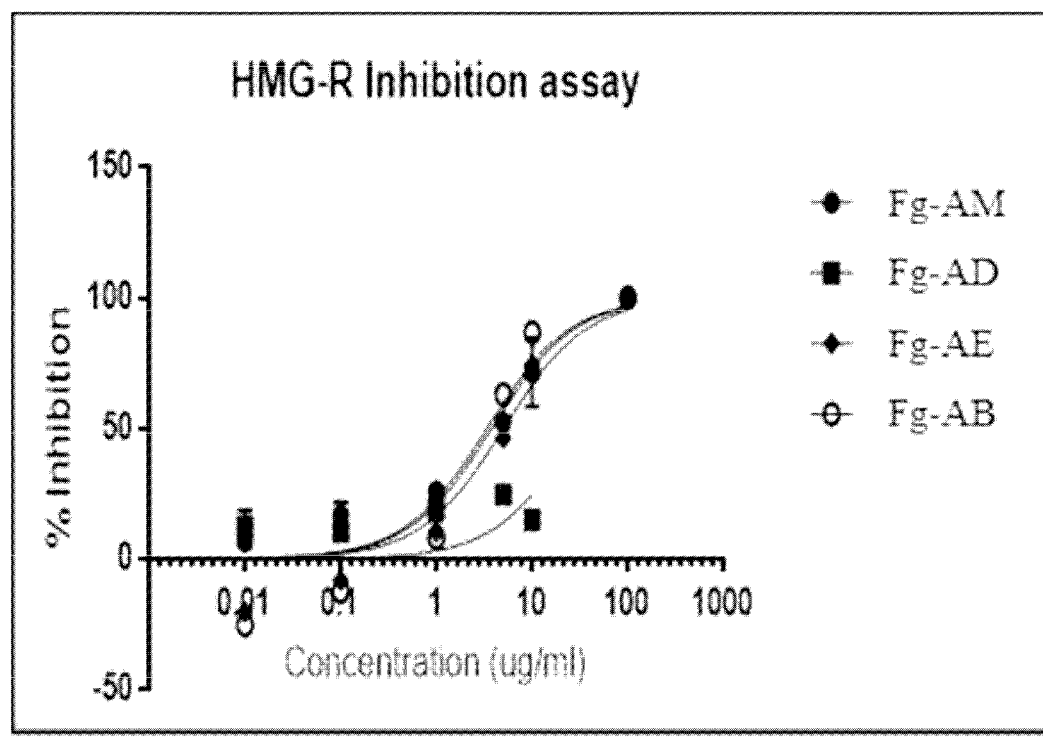
FIG. 1 is a graph for comparing HMG-CoA reductase inhibitory effects of a *Filipendula glaberrima* alcohol extract and solvent fractions fractionated therefrom.

Unless the context clearly indicates otherwise, all numbers, figures and/or expressions that represent ingredients, reaction conditions, polymer compositions and amounts of mixtures used in the specification are approximations that reflect various uncertainties of measurement occurring inherently in obtaining these figures, among other things. For this reason, it should be understood that, in all cases, the term "about" should modify all the numbers, figures and/or expressions. In addition, when numerical ranges are disclosed in the description, these ranges are continuous and include all numbers from the minimum to the maximum including the maximum within the range unless otherwise defined. Furthermore, when the range refers to an integer, it includes all integers from the minimum to the maximum including the maximum within the range, unless otherwise defined.

It should be understood that, in the specification, when a range is referred to regarding a parameter, the parameter encompasses all figures including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include numbers such as 10%, 11%, 12% and 13% as well as 30%, and any sub-ranges of 10% to 15%, 12% to 18%, or 20% to 30%, as well as any numbers, such as 10.5%, 15.5% and 25.5%, between appropriate integers that fall within the range.

Hereinafter, the present invention will be described in detail.

The present invention relates to a method for preparing a food composition and a therapeutic pharmaceutical composition containing a methanolic extract of the leaves of *Filipendula glaberrima* and a solvent extract solvent-fractionated therefrom and novel compounds 1 and 2 that are useful for lowering blood cholesterol levels and for ameliorating atherosclerosis by suppressing the activity of HMG-CoA reductase, which is a rate-limiting enzyme that regulates the speed of cholesterol synthesis, and by suppressing the formation of foam cells, which indicate an early stage of atherosclerosis.

The present invention also relates to an extract of *Filipendula glaberrima* having excellent effects of lowering blood cholesterol levels and of suppressing the formation of foam cells which are formed due to the introduction of oxidized LDL in macrophages, fractions thereof and active compounds isolated therefrom.

In another aspect, the composition, as an active ingredient, containing an alcoholic extract prepared from *Filipendula glaberrima* or a solvent fraction fractionated therefrom, or a novel compound 1 or 2 purely isolated from the *Filipendula glaberrima* ethyl acetate fraction by a series of isolation steps using column chromatography, is characterized by having excellent effects of suppressing the formation of foam cells which are formed due to the introduction of oxidized LDL in macrophages and of inhibiting HMG-CoA reductase activity.

In addition to this, the *Filipendula glaberrima* extract, fractions thereof and the active compounds isolated therefrom have excellent effects of scavenging free radicals and of inhibiting lipid peroxidation, and are thus useful for the prevention or treatment of aging caused by oxidative stress, and a variety of diseases such as cancer, brain diseases such as stroke and Parkinson's disease, heart diseases, ischemia, arteriosclerosis, skin diseases, digestive diseases, inflammation, rheumatism and autoimmune diseases.

The method for preparing the *Filipendula glaberrima* extract and fractions thereof according to the present invention, includes the steps of:

(Step 1) a first step of extracting *Filipendula glaberrima* with at least one extraction solvent selected from dichloromethane, acetone, an aqueous acetone solution, $C_{1-4}$ alcohol and a $C_{1-4}$ alcohol aqueous solution to obtain a solvent extract;

(Step 2) a second step of extracting the solvent extract obtained in the first step with water and ethyl acetate to obtain an ethyl acetate fraction; and (Step 3) a third step of fractionating the ethyl acetate fraction obtained in the second step through column chromatography to obtain novel compounds 1 to 2.

The *Filipendula glaberrima* used in the first step of obtaining the solvent extract may be any part of the plant growing aboveground or underground, and is preferably aboveground parts such as leaves, flowers, or stems of *Filipendula glaberrima*. The collected *Filipendula glaberrima* may be dried in the shade, or may be chopped, powderized or freeze-dried before use.

The extraction solvent used herein may be an ordinary organic solvent, and specifically may include at least one selected from dichloromethane, acetone, an aqueous acetone solution, $C_{1-5}$ alcohol and a $C_{1-5}$ alcoholic aqueous solution. More specifically, the extraction solvent may be dichloromethane, acetone, methanol, butanol, a mixed solvent thereof, or an aqueous solution thereof containing 20 to 80% by volume of water.

The respective steps of the method of preparing the *Filipendula glaberrima* extract and the fractions thereof according to the present invention are described in detail below.

An extraction solvent is added in an amount of 0.1 to 5 L, preferably 0.5 to 1.0 L, per kg of *Filipendula glaberrima*, and is allowed to stand at room temperature for 4 to 5 days. The extraction may be performed 1 to 5 times, or may be performed a greater number of times as necessary. In addition, the temperature during extraction is preferably 10° C. to 100° C., and more preferably room temperature, but is not limited thereto. The extraction time is preferably 1 to 7 days, and more preferably 3 to 7 days, but is not limited thereto. The obtained extract is filtered, evaporated under reduced pressure, and dried to obtain a solvent extract. The evaporation under reduced pressure is preferably conducted using a vacuum rotary evaporator, but is not limited thereto. In addition, drying may be performed using one selected from reduced-pressure drying, vacuum drying, boiling drying, spray drying, room-temperature drying, and freeze drying, but is not limited thereto.

In the second step of obtaining a fraction, the solvent extract obtained above is extracted with water and ethyl acetate to obtain an ethyl acetate fraction.

More specifically, the ethyl acetate fraction may be obtained by adding 1 to 5 L, preferably 1.5 to 2.0 L, of water to 1 kg of the solvent extract, adding 0.1 to 5 L of ethyl acetate, preferably 1.0 to 1.5 L, thereto, and sufficiently conducting extraction.

Further, in the present invention, the active compound can be sufficiently obtained even though the ethyl acetate extract is obtained by directly extracting the *Filipendula glaberrima* with ethyl acetate without the first step of obtaining the solvent extract using the organic solvent. However, in order to obtain a higher-purity active compound, it is preferable to sequentially perform the steps of obtaining the ethyl acetate fraction after step 1) of obtaining the solvent extract.

In the third step of obtaining the active compound, the ethyl acetate fraction obtained above is subjected to column chromatography.

The *Filipendula glaberrima* ethyl acetate fraction contains various active substances having hydroxy groups, such as triterpenes, tannins, and flavonoids.

The column chromatography is conducted by packing with a filler selected from the group consisting of silica gel, Sephadex, RP-18, polyamide, Toyopearl and XAD resin, and there is no particular limitation on the selection of filler in the present invention. Column chromatography is performed using an appropriate filler selected from the fillers described above. If necessary, chromatography may be performed several times using an appropriately selected filler. In particular, it is most preferable to perform an appropriate combination of column chromatography using Sephadex, RP-18 and silica gel as fillers.

Through the column chromatography process, each of the two novel compounds can be isolated.

In addition, the present invention is characterized by a pharmaceutical composition or a health food composition for treating, ameliorating and preventing hypercholesterolemia, or heart diseases or vascular diseases caused by hypercholesterolemia, containing, as active ingredients, an extract of *Filipendula glaberrima* or a fraction thereof.

The *Filipendula glaberrima* extract or the fraction thereof obtained by the isolation method of the active compounds described above contains the active compounds of the novel compound 1 to 2, thus exhibiting remarkable effects of treating, ameliorating and preventing hypercholesterolemia or heart diseases or vascular diseases caused by hypercholesterolemia.

In addition, the present invention is characterized by a pharmaceutical composition or a health food composition containing, as an active ingredient, a *Filipendula glaberrima* extract or a solvent fraction thereof.

The *Filipendula glaberrima* extract or the solvent fraction thereof exhibits excellent effects of inhibiting the activity of HMG-CoA reductase and of suppressing the formation of foam cells due to the incorporation of oxidized LDL in macrophages, thus being useful as an active ingredient for the pharmaceutical composition or the health food composition for lowering blood cholesterol levels.

That is, the disease or disorder that can be treated, prevented or alleviated through the effect of inhibiting the HMG-CoA reductase activity and the effect of suppressing the production of foam cells by each of the *Filipendula glaberrima* extract and the solvent fraction thereof specifically includes hypercholesterolemia, hyperlipidemia, arteriosclerosis, atherosclerosis, peripheral vascular diseases, dyslipidemia, hyperbetalipoproteinemia, hypoalphalipoproteinemia, hypercholesterolemia, hypertriglyceridemia, familial hypercholesterolemia, cardiovascular disorders, coronary heart diseases, coronary artery diseases, coronary vessel diseases, angina pectoris, ischemia, cardiac ischemia, thrombosis, myocardial infarction, stroke, peripheral vascular diseases, reperfusion injury, restenosis after angioplasty, hypertension, congestive heart failure, diabetes mellitus, diabetes-related vascular complications, obesity, endotoxemia and the like.

Hereinafter, various aspects of the present invention will be described.

In one aspect, the present invention provides a composition for preventing, ameliorating or treating a cardiovascular disease, containing an extract of *Filipendula glaberrima* or a fraction thereof as an active ingredient.

*Filipendula glaberrima*, the plant used herein, is a perennial plant that belongs to the Rosaceae family and is found only in Korea including Gyeongsang-do, Gyeonggi-do, Gangwon-do, and elsewhere. *Filipendula glaberrima* has almost no hairs in the whole body, and has erect, thin and long stems, and a height of about 1 m. The leaves grow alternately and are split into 3 to 7 lobes in the form of a palm, and petioles are long. The split sections are lanceolate, are sharp at the end, and are biserrate with deep depressions, and the length and width thereof are about 20 cm. The petiole has six pairs of small and large feather-shaped leaves that grow alternately with each other, and these leaves may be omitted, or only vestiges thereof may remain. White flowers bloom in cymose inflorescences on the ends of the stems and branches in June to August. Several small flowers gather in the shape of a duster. For this reason, this plant is called "duster herb". Young leaves are lightly boiled and seasoned, or vegetables are boiled in hot water and dried in the sun for use in a dried form.

As used herein, the term "extract" means any substance obtained by extracting ingredients from a natural product, regardless of the method of extraction or the type of ingredient. For example, broadly speaking, the extract includes a substance obtained by extracting an ingredient soluble in a solvent from a natural product using water or an organic solvent, a substance obtained by extracting only a specific ingredient from a natural product, or the like. In one embodiment of the present invention, the organic solvent is not particularly limited, and may be selected from $C_1$ to $C_5$ lower alcohols such as methanol, ethanol, isopropyl alcohol, n-propyl alcohol, n-butanol and isobutanol, polyhydric alcohols such as glycerol, ethylene glycol, propylene glycol and 1,3-butylene glycol, hydrocarbon solvents such as methyl acetate, ethyl acetate, benzene, n-hexane, diethyl ether, dichloromethane, chloroform, and non-polar organic solvents such as petroleum ether, methyl acetate, benzene, hexane, chloroform, methylene chloride, dimethyl ether, and ethyl acetate.

In another aspect, the present invention provides an antioxidant composition containing a *Filipendula glaberrima* extract or a fraction thereof as an active ingredient.

In another aspect, the present invention provides a composition for lowering cholesterol in blood containing a *Filipendula glaberrima* extract or a fraction thereof as an active ingredient.

In another aspect, the present invention provides a composition for inhibiting the production of foam cells containing a *Filipendula glaberrima* extract or a fraction thereof as an active ingredient.

In one aspect of the present invention, the *Filipendula glaberrima* extract is an extract of an aboveground or underground part of *Filipendula glaberrima*.

In one aspect of the present invention, the extract is an extract obtained by extraction using water, $C_1$-$C_5$ alcohol, acetone, an aqueous acetone solution or an aqueous $C_1$-$C_5$ alcohol solution.

In one aspect of the present invention, the $C_1$-$C_5$ alcohol includes at least one selected from the group consisting of methanol, ethanol, isopropyl alcohol, n-propyl alcohol, n-butanol and isobutanol.

In one aspect of the present invention, the concentrations of the aqueous $C_1$-$C_5$ alcohol solution and the aqueous acetone solution are each independently 10% to 90% (v/v).

In one aspect of the present invention, the *Filipendula glaberrima* extract may be present in an amount of 0.001 to 90% by weight based on the total weight of the composition. In one embodiment, the *Filipendula glaberrima* extract may be present in an amount of 0.001% by weight or more, 0.01% by weight or more, 0.1% by weight or more, 1% by weight or more, 1.1% by weight or more, 1.5% by weight or more, 2% by weight or more, 3% by weight or more, 5% by weight or more, 10% by weight or more, 20% by weight or more, or 30% by weight or more, based on the total weight of the composition. In addition, the *Filipendula glaberrima* extract may be present in an amount of 90% by weight or less, 85% by weight or less, 80% by weight or less, 70% by weight or less, 50% by weight or less, 40% by weight or less, 30% by weight or less, 20 by weight or less, 10% by weight or less, 5% by weight or less, 4% by weight or less, 3% by weight or less, 2% by weight or less, 1% by weight or less, 0.1% by weight or less or 0.05% by weight or less, based on the total weight of the composition.

In one aspect of the present invention, the fraction is an ethyl acetate fraction of the *Filipendula glaberrima* $C_1$-$C_5$ alcohol extract.

The composition for preventing, ameliorating or treating cardiovascular diseases according to one aspect of the present invention prevents, alleviates or treats the cardiovascular diseases through at least one of suppression of HMG-CoA reductase activity, suppression of foam cell production, and suppression of lipid peroxide production.

The antioxidant composition according to one aspect of the present invention exhibits an antioxidant effect through at least one of free radical scavenging, superoxide anion production inhibition, and lipid peroxide production inhibition.

The composition for ameliorating cardiovascular diseases, the antioxidant composition, the composition for lowering cholesterols or the composition for inhibiting the formation of foam cells according to one aspect of the present invention is a health food composition.

The composition for preventing, ameliorating or treating cardiovascular diseases according to one aspect of the present invention is a pharmaceutical composition.

In one aspect of the present invention, the pharmaceutical composition is formulated in the form of any one of injections, powders, granules, tablets, capsules, suspensions, emulsions, syrups, aerosols and external preparations.

In one aspect of the present invention, the cardiovascular disease may include at least one selected from the group consisting of hypercholesterolemia, hyperlipidemia, arteriosclerosis, atherosclerosis, peripheral vascular diseases, dyslipidemia, hyperbetalipoproteinemia, hypoalphalipoproteinemia, hypercholesterolemia, hypertriglyceridemia, familial hypercholesterolemia, cardiovascular disorders, coronary heart diseases, coronary artery diseases, coronary vessel diseases, angina pectoris, ischemia, cardiac ischemia, thrombosis, myocardial infarction, stroke, peripheral vascular diseases, reperfusion injury, restenosis after angioplasty, hypertension, congestive heart failure, diabetes mellitus, diabetes-related vascular complications, obesity, endotoxemia and the like.

The pharmaceutical composition of the present invention may be prepared in the form of a pharmaceutical preparation suitable for oral or parenteral administration by further including a suitable vehicle, excipient and/or diluent commonly used in the preparation of pharmaceuticals. In addition, pharmaceutical formulations may be prepared according to conventional methods using the pharmaceutical composition of the present invention. In the preparation of the formulations, the active ingredient may be mixed with the vehicle, diluted with the vehicle, or enclosed in the vehicle in the form of a capsule, sachet or other container. Thus, the formulations may be tablets, pills, powders, capsules, sachets, elixirs, suspensions, emulsions, liquids, syrups, aerosols, soft or hard gelatin capsules, solutions or suspensions for injection, ointments, creams, gels, lotions or the like.

Examples of suitable vehicles, excipients and diluents that can be included in the pharmaceutical compositions of the present invention include lactose, dextrose, sucrose, sorbitol, mannitol, calcium silicate, cellulose, methyl cellulose, microcrystalline cellulose, polyvinylpyrrolidone, water, methylhydroxybenzoate, propylhydroxybenzoate, talc, magnesium stearate and mineral oil. In addition, fillers, anticoagulants, lubricants, wetting agents, fragrances, emulsifiers, preservatives, and the like, which are commonly used in the preparation of formulations, may be further included. The pharmaceutical composition of the present invention may be formulated using methods well known in the art to provide rapid, sustained or delayed release of the active ingredient after administration to a mammal.

Examples of the route of administration of the pharmaceutical composition according to the present invention include, but are not limited to, oral, intravenous, intramuscular, intraarterial, intramedullary, intrathecal, intracardiac, transdermal, subcutaneous, intraperitoneal, intestinal, sublingual or topical administration.

The dosage of the pharmaceutical composition of the present invention may vary depending on the patient's condition and body weight, the severity of disease, the drug form, the administration route, and the duration of administration, and may be appropriately selected by those skilled in the art. The active ingredient relative to the patient's body weight may range from 0.001 mg/kg to 500 mg/kg, preferably 0.001 to 200 mg/kg. The administration may be performed once a day, or several times in a portionwise manner. The dosage does not limit the scope of the invention in any aspect.

In another aspect, the present invention provides a novel compound represented by the following Formula 1, an optical isomer thereof, a pharmaceutically acceptable salt thereof, a hydrate thereof or a solvate thereof:

[Formula 1]

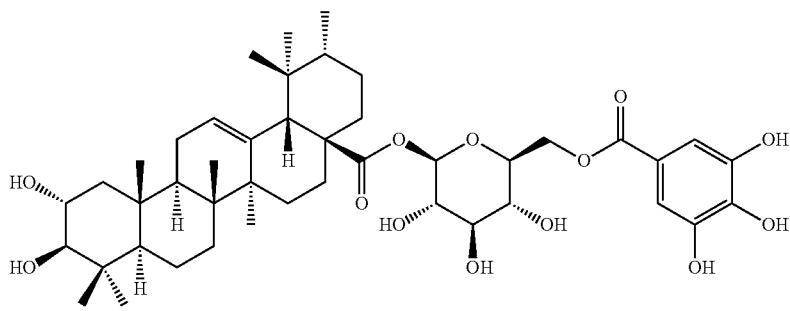

In another aspect, the present invention provides a novel compound represented by the following Formula 2, an optical isomer thereof, a pharmaceutically acceptable salt thereof, a hydrate thereof or a solvate thereof:

[Formula 2]

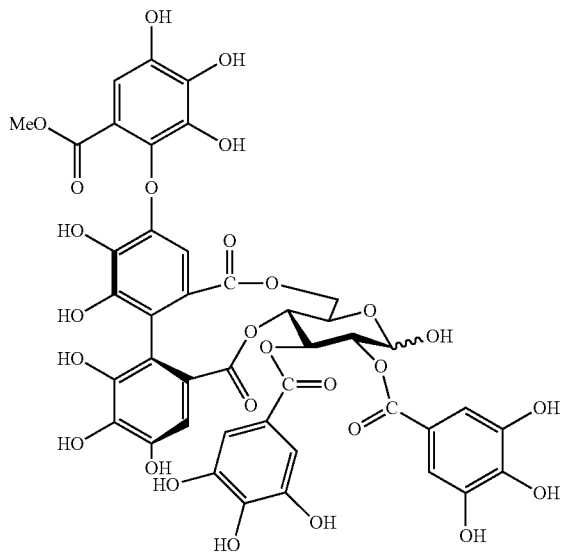

As used herein, the term "isomer" includes not only optical isomers (e.g., essentially pure enantiomers, essentially pure diastereomers or mixtures thereof), but also conformational isomers (i.e., isomers differing only in the angle of one or more chemical bonds), positional isomers (especially tautomers) or geometric isomers (e.g., cis-trans isomers).

As used herein, the term "essentially pure" means that, when used in connection with, for example, enantiomers or diastereomers, specific compounds provided as examples of the enantiomers or diastereomers are present in amounts of about 90% or more, preferably about 95% or more, more preferably about 97% or more, even more preferably about 98% or more, even still more preferably about 99% or more, and yet more preferably about 99.5% or more (w/w).

As used herein, the term "pharmaceutically acceptable" means that, by avoiding significant toxic effects when using a substance in common medical dosages in animals, more specifically in humans, the use of the substance in animals, more specifically in humans, can be approved or is approved by the government or a regulatory organization equivalent thereto, or is listed in the pharmacopeia or recognized to have been described in other general pharmacopeia.

As used herein, the term "pharmaceutically acceptable salt" refers to a salt according to an aspect of the present invention that is pharmacologically acceptable and exhibits the desired pharmacological activity of the parent compound thereof. The salt may include (1) acid addition salts formed from inorganic acids such as hydrochloric acid, hydrobromic acid, sulfuric acid, nitric acid or phosphoric acid; acid addition salts formed from organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfate, gluconic acid, glutamic acid, hydroxynaphthoic acid, salicylic acid, stearic acid, and muconic acid; or (2) salts formed by substitution of acidic protons present in the parent compound.

As used herein, the term "hydrate" refers to a compound to which water is bound and, broadly speaking, includes an included compound having no chemical bonding force between water and the compound.

As used herein, the term "solvate" refers to a higher-order compound formed between molecules or ions of a solute and molecules or ions of a solvent.

In another aspect, the present invention provides a composition for preventing, ameliorating or treating a cardiovascular disease containing the compound according to Formula 1 or 2, an optical isomer thereof, a pharmaceutically acceptable salt thereof, a hydrate thereof or a solvate thereof as an active ingredient.

In one embodiment, the composition for preventing, ameliorating or treating a cardiovascular disease may be a pharmaceutical composition.

In an embodiment of the present invention, the pharmaceutical composition is formulated in the form of any one of injections, powders, granules, tablets, capsules, suspensions, emulsions, syrups, aerosols and external preparations.

In an embodiment of the present invention, the cardiovascular disease may include at least one selected from the group consisting of hypercholesterolemia, hyperlipidemia, arteriosclerosis, atherosclerosis, peripheral vascular diseases, dyslipidemia, hyperbetalipoproteinemia, hypoalphalipoproteinemia, hypercholesterolemia, hypertriglyceridemia, familial hypercholesterolemia, cardiovascular disorders, coronary heart diseases, coronary artery diseases, coronary vessel diseases, angina pectoris, ischemia, cardiac ischemia, thrombosis, myocardial infarction, stroke, peripheral vascular diseases, reperfusion injury, restenosis after angioplasty, hypertension, congestive heart failure, diabetes mellitus, diabetes-related vascular complications, obesity and endotoxemia.

In an embodiment, the composition for ameliorating a cardiovascular disease may be a health food composition.

The health food composition according to the present invention contains an extract of *Filipendula glaberrima* or a solvent fraction fractionated therefrom and there is no particular limitation as to the type thereof. Examples of the food include drinks, meat, sausages, breads, biscuits, rice cakes, Sunsik (Korean ready-to-eat food prepared from grains), chocolate, candy, snacks, confectioneries, pizza, ramen, other noodles, gums, dairy products including ice cream, various soups, beverages, alcoholic beverages, vitamin complexes, dairy products and processed dairy products, and include all other functional health foods in the conventional sense. As an active ingredient, the extract of *Filipendula glaberrima* or the solvent fraction fractionated therefrom may be added alone to the food or may be used in conjunction with other foods or food ingredients, and may be suitably used according to conventional methods. The effective content may be appropriately determined according to the purpose of use (for prevention or amelioration), and may be present in a range of 0.001 to 70% by weight with respect to the total weight of the health food. However, in the case of long-term intake for health and hygiene purposes or for health control, the amount may be below the above range, and the active ingredient may be used in an amount above the range, since there is no problem in terms of safety. For example, in the case of preparing health beverages, the health drink may contain, in addition to the active ingredient, natural carbohydrates or flavoring agents as additives commonly used in the preparation of beverages. The natural carbohydrates may include conventional sugars, such as monosaccharides (e.g. glucose, fructose, etc.), disaccharides (e.g. maltose, sucrose, etc.) and polysaccharides (e.g., dextrin, cyclodextrin, etc.), and sugar alcohols such as xylitol, sorbitol and erythritol. The natural carbohydrate may be present in a range of 1 to 20% by weight, preferably 5 to 10% by weight, with respect to the total weight of the health food. The flavoring agent may include natural flavoring agents (thaumatin, stevia extract, rebaudioside A, glycyrrhizin, etc.) and synthetic flavoring agents (saccharin, aspartame, etc.). The health food may contain other nutrients, vitamins, minerals (electrolytes), flavors (synthetic or natural flavors), colorants, pectic acids and salts thereof, alginic acids and salts thereof, organic acids, protective colloidal thickeners, pH-adjusting agents, stabilizers, preservatives, glycerin, alcohol, carbonic acid used in carbonated beverages, and the like. In addition, it may contain flesh for the production of natural fruit juices, fruit juice beverages and vegetable beverages. The content of these additives is not particularly limited, but may fall within a range of 0.1 to 20% by weight with respect to the total weight of the health food.

In another aspect, the present invention provides a health food composition for obtaining an antioxidant effect containing the compound according to Formula 1 or 2, an optical isomer thereof, a pharmaceutically acceptable salt thereof, a hydrate thereof or a solvate thereof as an active ingredient.

In another aspect, the present invention provides a health food composition for lowering blood cholesterol levels containing the compound according to Formula 1 or 2, an optical isomer thereof, a pharmaceutically acceptable salt thereof, a hydrate thereof or a solvate thereof as an active ingredient.

In another aspect, the present invention provides a health food composition for inhibiting the formation of foam cells containing the compound according to Formula 1 or 2, an optical isomer thereof, a pharmaceutically acceptable salt thereof, a hydrate thereof or a solvate thereof as an active ingredient.

In another aspect, the present invention provides a compound according to Formula 1 or 2, an optical isomer thereof, a pharmaceutically acceptable salt thereof, a hydrate thereof or a solvate thereof, wherein the compound according to Formula 1 or 2 is an ingredient isolated from *Filipendula glaberrima*.

Hereinafter, the present invention will be described in more detail with reference to specific examples. However, the following examples are provided only for illustration of the present invention, and should not be construed as limiting the scope of the present invention.

EXAMPLE

Example 1. Preparation of Extracts or Fractions of *Filipendula glaberrima* Leaves 6 L of methanol was added to collected leaves of *Filipendula glaberrima* (dry weight of 840 g), and extraction was conducted at room temperature for one week. After this process was repeated three times, the resulting product was filtered and concentrated to dryness with a rotary concentrator at 40° C. to obtain 194.6 g of a methanol extract. The methanol extract was suspended with 2,000 mL of water and then was extracted with dichloromethane (2,000 ml×3). The aqueous layer was extracted with ethyl acetate (2,000 mL×3) to obtain an ethyl acetate fraction. Then, the aqueous layer was again extracted with butanol (2,000 mL×3) to obtain a butanol fraction.

Example 2. Preparation of Extracts or Fractions of *Filipendula glaberrima* Stems 2 L of methanol was added to collected stems of *Filipendula glaberrima* (dry weight of 300 g), and extraction was conducted at room temperature for one week. After this process was repeated three times, the resulting product was filtered and concentrated to dryness with a rotary concentrator at 40° C. to obtain 42.13 g of a methanol extract. The methanol extract was suspended with 400 mL of water and then was extracted with dichloromethane (400 mL×3). The aqueous layer was extracted with ethyl acetate (400 mL×3) to obtain an ethyl acetate fraction. Then, the aqueous layer was again extracted with butanol (400 mL×3) to obtain a butanol fraction.

Example 3. Preparation of Extracts or Fractions of *Filipendula glaberrima* Flowers 600 mL of methanol was added to collected flowers of *Filipendula glaberrima* (dry weight of 67.8 g), and extraction was conducted at room temperature for one week. After this process was repeated three times, the resulting product was filtered and concentrated to dryness with a rotary concentrator at 40° C. to obtain 25.3 g of a methanol extract.

The methanol extract was suspended with 250 mL of water and was then extracted with dichloromethane (250 mL×3). The aqueous layer was extracted with ethyl acetate (250 mL×3) to obtain an ethyl acetate fraction. Then, the aqueous layer was again extracted with butanol (250 mL×3) to obtain a butanol fraction.

Example 4. Isolation of Novel Compounds 1 and 2 From Ethyl Acetate Fractions 12.5 g of the ethyl acetate fraction of the *Filipendula glaberrima* leaves obtained in Example 1 was subjected to column chromatography (7×26 cm) using Sephadex LH-20 column chromatography. Methanol was used as a developing solvent, and the obtained fractions were observed with a normal-phase silica gel TLC (developing solvent: dichloromethane/methanol/water=50/10/1), and then compounds with similar polarity were collected and divided into 11 subfractions (EA-EI1).

The subfraction E3 (4.1 g) was dissolved in methanol, the insoluble solid was filtered, and the filtrate was repeatedly subjected to column chromatography and reverse-phase silica gel column chromatography (40% methanol) to obtain 8.7 mg of a novel compound 1.

The subfraction E8 (792.9 mg) was divided into three subfractions (E8a to E8c) using methanol as a developing solvent by Sephadex LH-20 column chromatography. The subfraction E8b (721.2 mg) was subjected to column chromatography using 40% methanol as a developing solvent and using reverse-phase silica gel as a stationary phase. Similar compounds were collected by TLC and divided into 8 subfractions (E8b1 to E8b8). A novel compound 2 (20.6 mg) was obtained from the first fraction, E8b1 (543.7 mg), using Toyopearl HW-40C and preparative HPLC.

Example 5. Structural Characterization of Novel Compounds

The NMR spectra of the novel compounds isolated from the ethyl acetate fraction fractionated from the *Filipendula glaberrima* alcohol extract were obtained using 400 MHz ($^1$H) and 100 MHz ($^{13}$C), and the chemical shift of each peak was expressed as a relative value for trimethylsilane, an internal standard. $^1$H NMR, $^{13}$C NMR, HSQC and HMBC spectra for structural analysis of the novel compounds are shown in FIGS. 5 to 12.

(1) Structure Determination of Compound 1

The chemical properties of Compound 1 of the present invention are as follows.

Amorphous white powder

HR-ESI-TOP-MS (positive-ion mode) m/z 825.4020 [M+Na]$^+$ (calcd. for 825.4037, $C_{43}H_{62}O_{14}Na$)

$^1$H NMR (400 MHz, $CD_3OD$): δ0.665 (s, 3H, H-26), 0.761 (s, 6H, H-25, 24), 0.936 (d, 3H, J=6.8 Hz, H-30), 0.982 (s, 3H, H-23), 1.194 (s, 3H, H-29), 1.296 (s, 3H, H-27), 2.566 (s, 1H, H-18), 2.886 (d, 1H, J=9.6 Hz, H-3), 3.368-3.484 (3H, m, H-2', 3', 4'), 3.558-3.593 (m, 1H, H-2), 3.672 (m, 1H, H-5'), 4.337 (dd, 1H, J=5.6, 12.0 Hz, H-6a'), 4.405 (dd, 1H, J=2.0, 12.0 Hz, H-6b'), 5.290 (brt, 1H, H-12), 5.402 (d, 1H, J=8.0 Hz, H-1'), 7.095 (s, 2H, H-2", 6").

$^{13}$C NMR (100 MHz, $CD_3OD$): δ16.55 (C-30), δ16.55 (C-25), 17.39 (C-24), 17.94 (C-26), 17.41 (C-6), 24.66 (C-11), 24.81 (C-27), 26.42 (C-16), 26.93 (C-29), 27.05 (C-21), 29.25 (C-15, 23), 33.88 (C-7), 38.42 (C-22), 38.95 (C-10), 40.38 (C-4), 41.20 (C-8), 42.39 (C-14), 42.60 (C-20), 48.35 (C-1), 48.78 (C-9, overlapped with solvent), 49.63 (C-17), 54.60 (C-18), 56.57 (C-5), 65.05 (C-6'), 69.53 (C-2), 71.45 (C-4'), 73.65 (C-2'), 73.78 (C-19), 75.77 (C-5'), 78.14 (C-3'), 95.51 (C-1'), 110.39 (C-2", 6"), 121.28 (C-1"), 129.70 (C-12), 139.46 (C-4"), 139.84 (C-13), 146.42 (C-3", 5"), 168.56 (C-7"), 178.85 (C-28).

Compound 1 is a ursane-type triterpene having a structure in which hydroxy groups are substituted at positions 2 and 19, respectively, and a substituent having a galloyl group bonded to glucose 6 is ester-bonded at position 28 of ursolic acid. It is a novel compound that is isolated from nature and elucidated as to the structure thereof for the first time in this study.

(2) Structure Determination of Compound 2

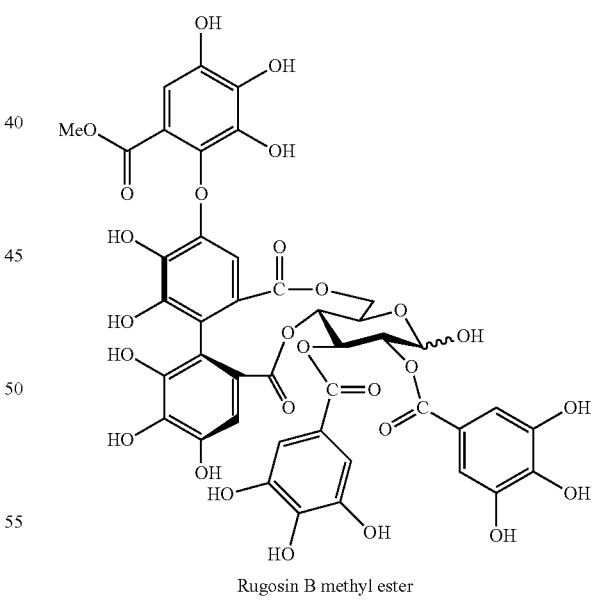

Rugosin B methyl ester

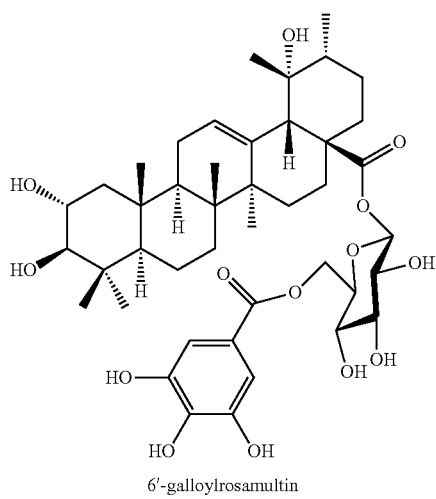

6'-galloylrosamultin

The chemical properties of Compound 2 of the present invention are as follows.

Amorphous pale brown powder

HR-ESI-TOP-MS (positive-ion mode) m/z 991.1015 [M+Na]$^+$ (calcd. for 991.1028, $C_{42}H_{32}O_{27}Na$)

$^1$H NMR (400 MHz, $CD_3OD$): δ3.741, 3.752 (s, H$_\alpha$—OMe, H$_\beta$—OMe), 3.769, 3.848 (d, J=13.6 Hz, H$_\alpha$-glc6, H$_\beta$-glc6), 4.180 (m, H$_\beta$-glc5), 4.609 (m, H$_\alpha$-glc5), 5.068 (d, J=7.6 Hz, $H_\beta$-glc1), 5.099 (m, $H_\alpha$-glc4, $H_\beta$-glc4), 5.113 (dd, J=3.6, 10.0 Hz, $H_\alpha$-glc2), 5.187 (br t, J=7.6, 8.4 Hz, $H_\beta$-glc2), 5.252 (dd, J=6.8, 13.6 Hz, $H_\alpha$-glc6), 5.338 (dd, J=6.0, 13.6 Hz, $H_\beta$-glc6), 5.477 (d, J=3.6 Hz, $H_\alpha$-glc1), 5.852 (t, J=9.6 Hz, $H_\beta$-glc3), 5.857 (t, J=10.0 Hz, $H_\alpha$-glc3), 6.192, 6.481 (s, β-anomer valoneoyl-3, 3'), 6.198, 6.522 (s, α-anomer valoneoyl-3, 3'), 6.913, 7.018 (s, β-anomer galloyl-2, 6), 6.948, 7.038 (s, α-anomer galloyl-2, 6), 6.953 (s, β-anomer valoneoyl-6"), 7.062 (s, α-anomer valoneoyl-6").

$^{13}C$ NMR (100 MHz, $CD_3OD$): δ52.48 (C-OMe), 64.23, 64.31 ($C_{\alpha,\beta}$-glc6), 67.49 ($C_\alpha$-glc5), 71.66 ($C_\beta$-glc4), 71.95, 72.01 ($C_\alpha$-glc3,4), 72.69 ($C_\beta$-glc2), 73.44 ($C_\alpha$-glc2), 74.31 ($C_\beta$-glc5), 74.70 ($C_\beta$-glc3), 91.72 ($C_\alpha$-glc1), 97.01 ($C_\beta$-glc1), 106.02, 106.08, 108.08 ($C_{\alpha,\beta}$-valoneoyl-3, 3'), 109.93 ($C_{\alpha,\beta}$-valoneoyl-6"), 110.34, 110.39, 110.44 ($C_{\alpha,\beta}$-galloyl-2,6), 115.06 ($C_{\alpha,\beta}$-valoneoyl-1), 116.22, 118.53 ($C_{\alpha,\beta}$-valoneoyl-1,1'), 120.56, 120.85, 120.80, 120.87 ($C_{\alpha,\beta}$-galloyl-1, 1'), 125.67, 125.74, 125.91, 125.93 ($C_{\alpha,\beta}$-valoneoyl-2, 2'), 137.59, 137.61, 137.66, 137.69 ($C_{\alpha,\beta}$-valoneoyl-5, 4"), 138.27 ($C_{\alpha,\beta}$-valoneoyl-5'), 139.94, 139.98, 140.01, 140.15 ($C_{\alpha,\beta}$-galloyl-4, 4'), 140.82, 140.87 ($C_{\alpha,\beta}$-valoneoyl-2", 3"), 143.83 ($C_{\alpha,\beta}$-valoneoyl-5"), 144.97 ($C_{\alpha,\beta}$-valoneoyl-6), 145.33, 145.36 ($C_{\alpha,\beta}$-valoneoyl-6'), 145.99 ($C_{\alpha,\beta}$-valoneoyl-4), 146.19, 146.21 ($C_{\alpha,\beta}$-galloyl-3, 5), 146.35, 146.38 ($C_{\alpha,\beta}$-galloyl-3', 5'), 147.61, 147.67 ($C_{\alpha,\beta}$-valoneoyl-4'), 167.10 ($C_\beta$-galloyl-7), 167.47 ($C_\alpha$-galloyl-7), 167.63 ($C_{\alpha,\beta}$-valoneoyl-7"), 167.70 ($C_\beta$-galloyl-7'), 167.93 ($C_\alpha$-galloyl-7'), 169.14, 169.22 ($C_\beta$-valoneoyl-7, 7'), 169.29, 169.40 ($C_\alpha$-valoneoyl-7, 7').

Compound 2 is a hydrolysable tannin having a structure in which galloyl groups are bonded to glucose 2 and 3, respectively, valoneoyl groups are bonded to glucose 4 and 6, respectively, and a methyl group is ester-bonded at the valoneoyl group 7, and is a tautomer in which an α-anomer and a β-anomer having an unsubstituted hydroxyl group at the position 1 of glucose moiety. Compound 2 is a compound produced through chemical changes for structural analysis in prostratin B isolated from *Euphorbia prostrata* and *Loropetalum chinense*. It is a novel compound that is isolated from nature and elucidated as to the structure thereof for the first time in this study.

Experimental Example 1. Experiment on HMG-CoA Reductase Inhibitory Effect

1) Reagents and Equipment

Sodium monophosphate, sodium diphosphate, DL-HMG-CoA sodium salt hydrate, reduced β-nicotinamide adenine dinucleotide 2'-phosphate (NADPH), pravastatin, NaCl, DL-dithiothreitol (DTT), dimethylsulfoxide (DMSO), ethylenediamine tetraacetic acid (EDTA), and HMG-CoA reductase (712 μg/ml) were purchased from Sigma-Aldrich (St. Louis, Mo.). Transparent 96-well plates were purchased from SPL Lifesciences (Pocheon). A VERSA Max™ microplate reader from Molecular Devices was used.

2) Method for Detecting HMG-CoA Reductase Inhibitory Effect

The HMG-CoA reductase inhibitory effect was evaluated using a slightly modified mode of Perchellet's assay (*Int. J. Mol. Med.*, 2009, 24, 633). The sample for detection was dissolved in DMSO before use. That is, 100 mM NaCl, 1 mM EDTA, 10 mM DTT and 10 mM NADPH were added to a 96-well plate, the sample for detection was added to a 100 mM sodium phosphate buffer (pH 6.8), and 10.2 μg/ml of HMG-CoA reductase (8 mM, final concentration) was added thereto to start the reaction.

The activity of HMG-CoA reductase was compared and analyzed by recording the absorbance at 340 nm at 37° C. for 10 minutes using a VERSA Max™ microplate reader. DMSO was used as a control, and 100 μM pravastatin was used as a positive control. The experiment was repeated three times.

The effects of inhibiting HMG-CoA reductase by the alcoholic extract of the *Filipendula glaberrima* leaves and the dichloromethane fraction (308-44AD), ethyl acetate fraction (308-44AE) and butanol fraction (308-44AB), obtained through solvent fractionation therefrom, were detected at various concentrations. The detection results are shown in Table 1 below and in FIG. 1.

TABLE 1

| Sample | | HMG-CoA reductase inhibitory activity, $IC_{50}$ (μg/ml) |
|---|---|---|
| Methanol extract (Fg-AM) | | 2.86 ± 0.24 |
| Dichloromethane fraction (Fg-AD) | | 19.8 ± 2.73 |
| Ethyl acetate fraction (Fg-AE) | | 1.73 ± 0.23 |
| Butanol fraction (Fg-AB) | | 1.73 ± 0.30 |
| 30% ethanol extract (Fg-A-30EtOH) | | 3.67 ± 0.78 |
| 50% ethanol extract (Fg-A-50EtOH) | | 3.29 ± 0.58 |
| 70% ethanol extract (Fg-A-70EtOH) | | 3.38 ± 0.55 |
| Compound 1 (μM) | | 175.2 ± 2.2 |
| Compound 2 (μM) | | 1.46 ± 0.22 |
| Reference drug | Pravastatin (μM) | 0.40 ± 0.04 |

*Data are expressed as mean ± standard error.

As can be seen from Table 1 and FIG. 1, the *Filipendula glaberrima* extract or solvent fractions thereof have remarkably excellent $IC_{50}$ values against HMG-CoA reductase of 1.46 to 3.67 μg/ml. The reference drug used to compare the effects of the extracts was pravastatin, which is currently used in clinical practice. The $IC_{50}$ value of the reference drug was 0.40±0.04 μM. Although it is difficult to compare the efficacy with a single substance, the *Filipendula glaberrima* extract or fractions thereof exhibited considerably potent effects when taking into consideration the fact that the *Filipendula glaberrima* extract was a mixture.

Figure 2:
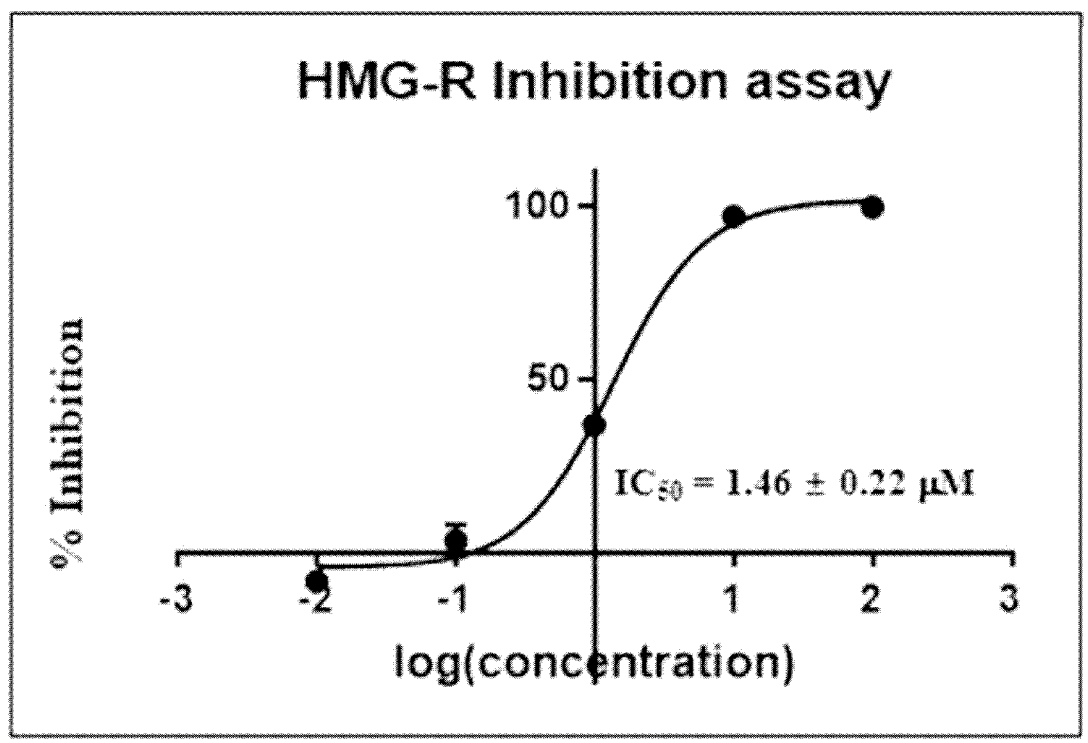
FIG. 2 is a graph showing 50% inhibition concentration ($IC_{50}$) against HMG-CoA reductase of novel compound 2, purely isolated from a *Filipendula glaberrima* ethyl acetate fraction.

Meanwhile, novel compound 1 has an $IC_{50}$ value against HMG-CoA reductase of 175.2±2.2 μg/ml, as shown in Table 1, and the novel compound 2 has an excellent $IC_{50}$ value against HMG-CoA reductase of 1.46±0.22 μg/ml, as shown in Table 1 and FIG. 2. This means that the compounds exhibit excellent effects and thus have high potential for the development into natural medicines as compounds isolated from edible natural products for the development of materials that can replace statin-based drugs, which have been reported to cause many side effects.

Experimental Example 2. Experiment on Antioxidant Effect of *Filipendula glaberrima* Extract 1) Detection of DPPH Radical Scavenging Effect Free-radical scavenging action (Blois et al., Nature, 1958, 181, 1199) was evaluated as $IC_{50}$ by adding the test samples obtained in Examples to 190 μl of a 100 μM 1,1-diphenyl-2-picryl hydrazyl (DPPH) ethanol solution, conducting reaction at 37° C. for 30 minutes and measuring the absorbance at 515 nm. $IC_{50}$ means a concentration ($SC_{50}$) at which 50% of free-radical scavenging is obtained when calculating the free-radical scavenging activity. Data are expressed as an average of measurements conducted in triplicate.

2) Detection of Xanthine/Xanthine Oxidase-Induced Superoxide Anion ($O_2^-$) Scavenging Effect by *Filipendula glaberrima* Extract The following method of Toda et al. (*Planta, Med.* 57:8, 1991) was conducted to evaluate the effect of inhibiting the production of superoxide anions which are produced by the reaction of xanthine and xanthine oxidase (XOD). Specifically, 0.1 mM xanthine, 0.1 mM EDTA, 50 μg/ml of bovine serum albumin (BSA), 25 mM nitroblue tetrazolium (NBT), a 40 mM $Na_2CO_3$ solution, a test sample solution diluted at each concentration and a solution with a final volume of 200 μl containing $1.4 \times 10^{-3}$ unit XOD were mixed and reacted at 25° C. for 20 minutes. After stopping the reaction by adding 6.6 μl of 6 mM $CuCl_2$ to the reaction solution, the absorbance of the formed formazan was measured at 560 nm and the result of comparison of the xanthine/xanthine oxidase-induced superoxide anion scavenging effect was calculated as $IC_{50}$. $IC_{50}$ refers to a concentration ($SC_{50}$) at which 50% of xanthine/xanthine oxidase-induced superoxide anion scavenging is obtained when calculating the xanthine/xanthine oxidase-induced superoxide anion scavenging activity, and data are expressed as an average of measurements conducted in triplicate.

3) Effect of Inhibiting Formation of Lipid Peroxide by *Filipendula glaberrima* Extract The lipid peroxide production inhibitory effect (LPO) of the extract and the isolated compounds were tested. Lipid peroxide is a substance produced by peroxidation of lipids through various oxidation reactions. Reactive oxygen species, free radicals and the like oxidize phospholipids of cell membranes containing great amounts of unsaturated fatty acids, producing lipid peroxides in the cell membranes. When the lipid peroxides are accumulated in the cell membranes, the fluidity and functionality of the cell membrane are deteriorated, resulting in local disorders in tissues such as inhibition of cell functions and changes in cell structures.

Therefore, the effects of inhibiting lipid peroxide production by the *Filipendula glaberrima* leaf and stem extracts and the isolated compounds were measured as follows. The animals used in the experiment were male Sprague-Dawley rats, and only water was supplied for 24 hours before the experiment. The experiment was conducted according to the guidelines for the management and use of laboratory animals, approved by the Animal Research Ethics Committee of the Korea Institute of Science and Technology (Approval number: KISTIACUC-2018-081). The experimental animals were subjected to respiratory anesthesia with isoflurane, and dissected and a 0.15 M ice-cold KCl solution was perfused through the liver portal vein to remove blood from the liver and extract the liver. A liver homogenate was prepared by homogenizing with a KCl solution in an amount weighing 10 times the weight of the liver, and the protein concentration was quantified by the Bradford protein method using bovine serum albumin as a standard (Bradford, M M *Anal. Biochem.* 72, 248, 1976). The lipid peroxidation test was performed using a slightly modified mode of the method of Sanz et al. (Sanz, M. J., et al., *Xenobiotica* 24, 689-69, 1994). 50 mM Tris-HCl buffer (pH 7.5) was added to 300 μl of a liver homogenate (11 mg protein/ml), 10 μM $FeSO_4$, 10 μl of a test drug and 0.4 mM ascorbic acid to adjust the total volume to 1 ml, and then the resulting mixture was incubated at 37° C. for 30 minutes. After incubation, 2 ml of a TBA-TCA solution (0.375% thiobarbituric acid, 15% trichloroacetic acid, 0.25 N HCl, 0.01% butylated hydroxytoluene) was added thereto, allowed to react at 95° C. for 30 minutes and then cooled and centrifuged (5,000×g) for 10 minutes, and the absorbance of the supernatant was measured at 535 nm. Silymarin, resveratrol and quercetin were used as reference drugs to compare the lipid peroxidation inhibitory effect. As a control, DMSO was used, instead of the test drug, and the concentration ($IC_{50}$) of the sample required to inhibit the formation of lipid peroxide by 50% was measured, and the results are shown in Table 2 below.

TABLE 2

|  | Sample | $SC_{50}$ (μg/ml) DPPH radical | $SC_{50}$ (μg/ml) Superoxide anion radical ($O_2^-$) | $IC_{50}$ (μg/ml) LPO |
|---|---|---|---|---|
|  | *Filipendula glaberrima* leaf MeOH | 11.07 ± 0.97 | 18.07 ± 3.89 | 26.28 ± 2.14 |
|  | *Filipendula glaberrima* leaf $CH_2Cl_2$ fraction | 38.36 ± 3.10 | >50 | 75.23 ± 2.57 |
|  | *Filipendula glaberrima* leaf EtOAc fraction | 4.62 ± 0.28 | 4.07 ± 0.08 | 9.67 ± 0.14 |
|  | *Filipendula glaberrima* leaf BuOH fraction | 5.25 ± 0.13 | 4.64 ± 0.23 | 18.77 ± 0.58 |
|  | *Filipendula glaberrima* stem MeOH | 45.51 ± 5.60 | >50 | >50 |
|  | *Filipendula glaberrima* stem $CH_2Cl_2$ fraction | >50 | >50 | >50 |
|  | *Filipendula glaberrima* stem EtOAc fraction | 4.28 ± 0.54 | 45.00 ± 2.98 | 5.69 ± 3.01 |
|  | *Filipendula glaberrima* stem BuOH fraction | 28.06 ± 1.53 | >50 | 69.44 ± 5.32 |
|  | *Filipendula glaberrima* flower MeOH | 4.83 ± 1.14 | 35.95 ± 2.38 | 6.04 ± 1.66 |
|  | *Filipendula glaberrima* flower $CH_2Cl_2$ | 27.64 ± 1.11 | >50 | 76.02 ± 8.79 |
|  | *Filipendula glaberrima* flower EtOAc fraction | 3.24 ± 0.32 | 31.23 ± 4.12 | 6.92 ± 0.32 |
|  | *Filipendula glaberrima* flower BuOH fraction | 4.68 ± 1.06 | 35.64 ± 4.40 | 7.61 ± 0.08 |
|  | Compound 1 (μM) | 47.88 ± 0.01 |  | 89.01 ± 3.69 |
|  | Compound 2 (μM) | 3.62 ± 0.57 | 41.10 ± 2.24 | 7.99 ± 0.05 |
| Reference drug | Resveratrol (μM) | 56.24 ± 5.22 | >50 | 35.64 ± 0.01 |
|  | Quercetin (μM) | 19.04 ± 2.25 | >50 | 29.57 ± 1.32 |
|  | Vit. C (μM) | 29.27 ± 2.49 | >50 | — |
|  | Silymarin | 43.22 ± 2.58 | >50 | 98.7 ± 0.02 |
|  | Trolox (μM) | 47.50 ± 0.41 | >50 | >50 |

Regarding the DPPH radical-scavenging activity, superoxide anion radical-scavenging activity and lipid peroxide production inhibitory activity, which were detected as antioxidant activities important for vascular protection, the *Filipendula glaberrima* extracts and solvent fractions also exhibited excellent antioxidant effect, as shown in Table 2. That is, the ethyl acetate fraction and the butanol fraction, which are solvent fractions from the *Filipendula glaberrima* alcohol extract, have 50% radical-scavenging activity ($SC_{50}$) of 4.07 to 6.27 µg/ml, and thus exhibit excellent effect compared to radical-scavenging activity ($SC_{50}$) of ascorbic acid, quercetin and resveratrol, which are well-known antioxidant substances, used as reference drugs. Regarding the effect of inhibiting the production of lipid peroxide using rat liver homogenates, the 50% inhibitory activity ($IC_{50}$) of the ethyl acetate fraction solvent-fractionated from the *Filipendula glaberrima* alcohol extract was 9.67±0.14 µg/ml, which was about 10 times higher than 98.7±0.02 µg/mL, the inhibitory activity ($IC_{50}$) of silymarin used as a liver protective agent, and was about 3 times higher than 29.57±1.32 µg/mL, the inhibitory activity ($IC_{50}$) of quercetin.

Figure 3:
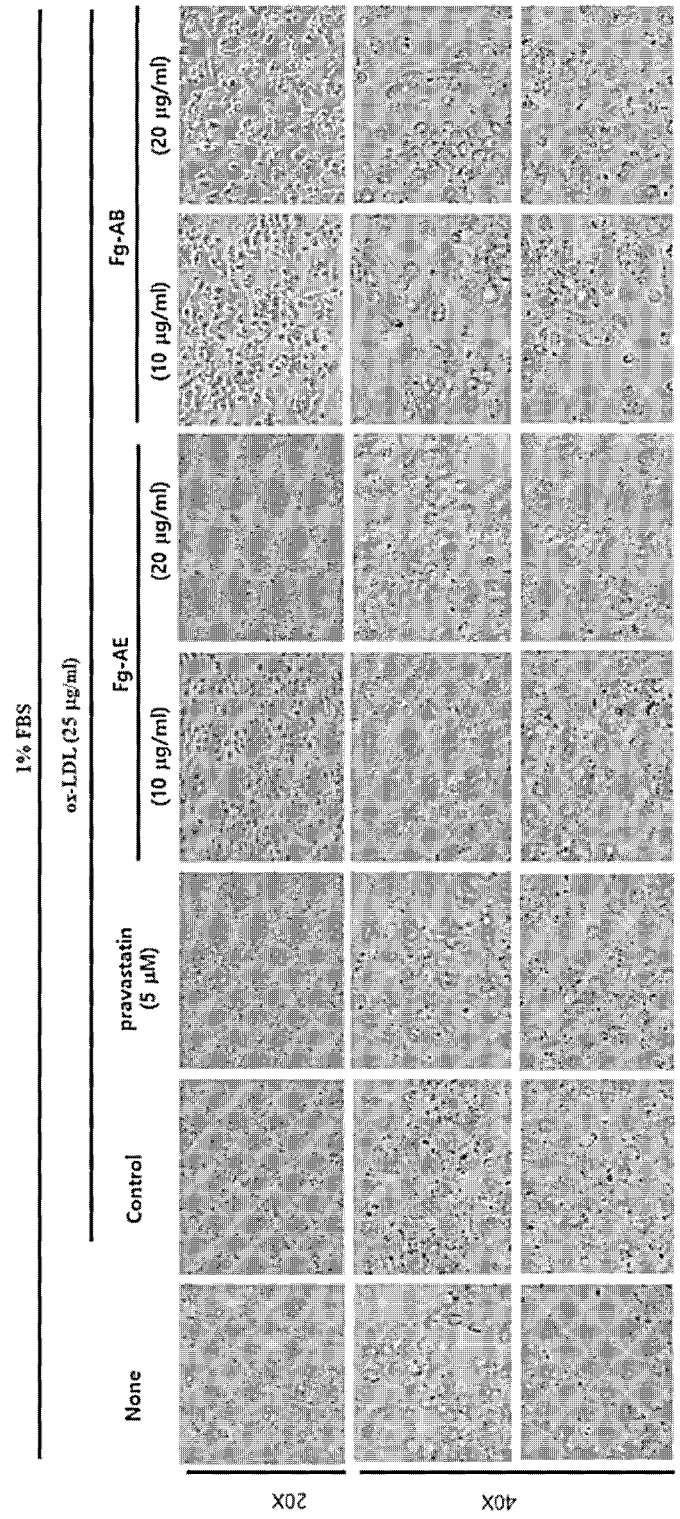
FIG. 3 is a graph showing the degree of lipid accumulation in cells using Oil red O, indicating the effect of suppressing the production of foam cells by the introduction of oxidized LDL in macrophages for the solvent fractions fractionated from the *Filipendula glaberrima* alcohol extract.
Figure 4:
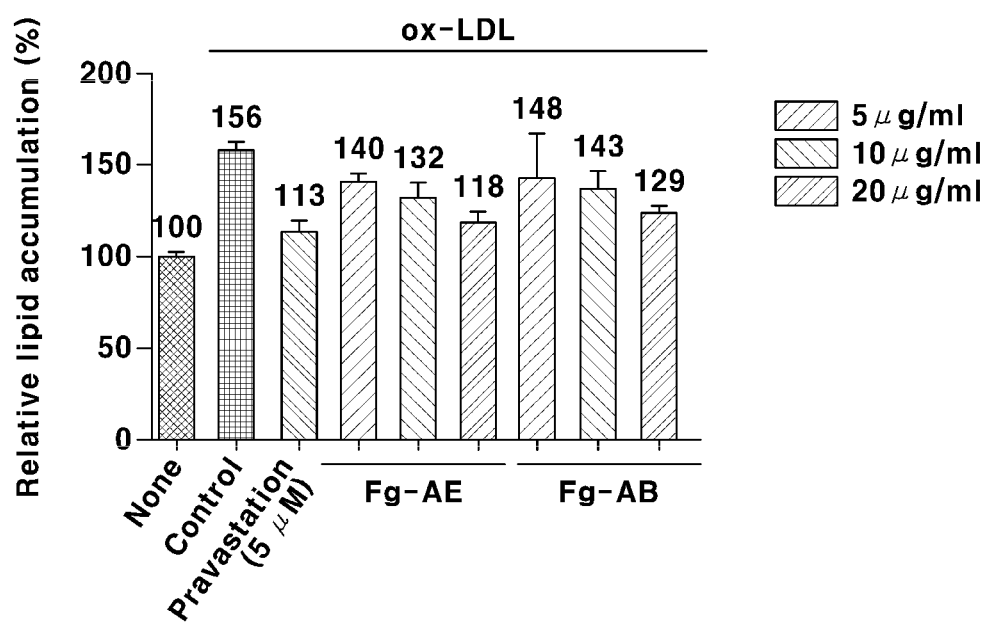
FIG. 4 is a bar graph showing the effect of suppressing the production of foam cells by the introduction of oxidized LDL in macrophages at different concentrations of the solvent fractions fractionated from the *Filipendula glaberrima* alcohol extract.
Figure 5:
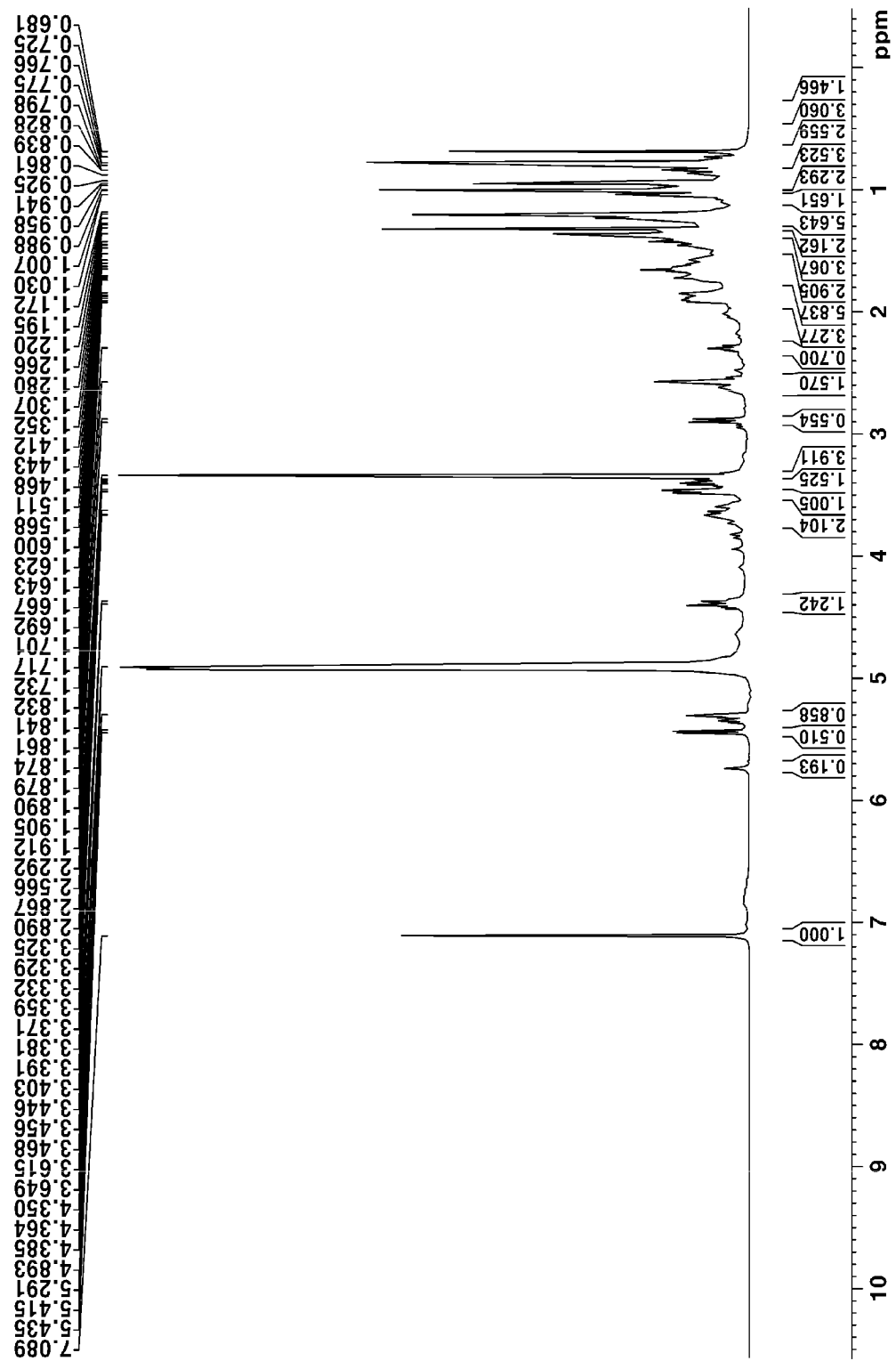
FIG. 5 is a $^1$H NMR of novel compound 1, purely isolated from the ethyl acetate fraction fractionated from the *Filipendula glaberrima* alcohol extract using various kinds of column chromatography.
Figure 6:
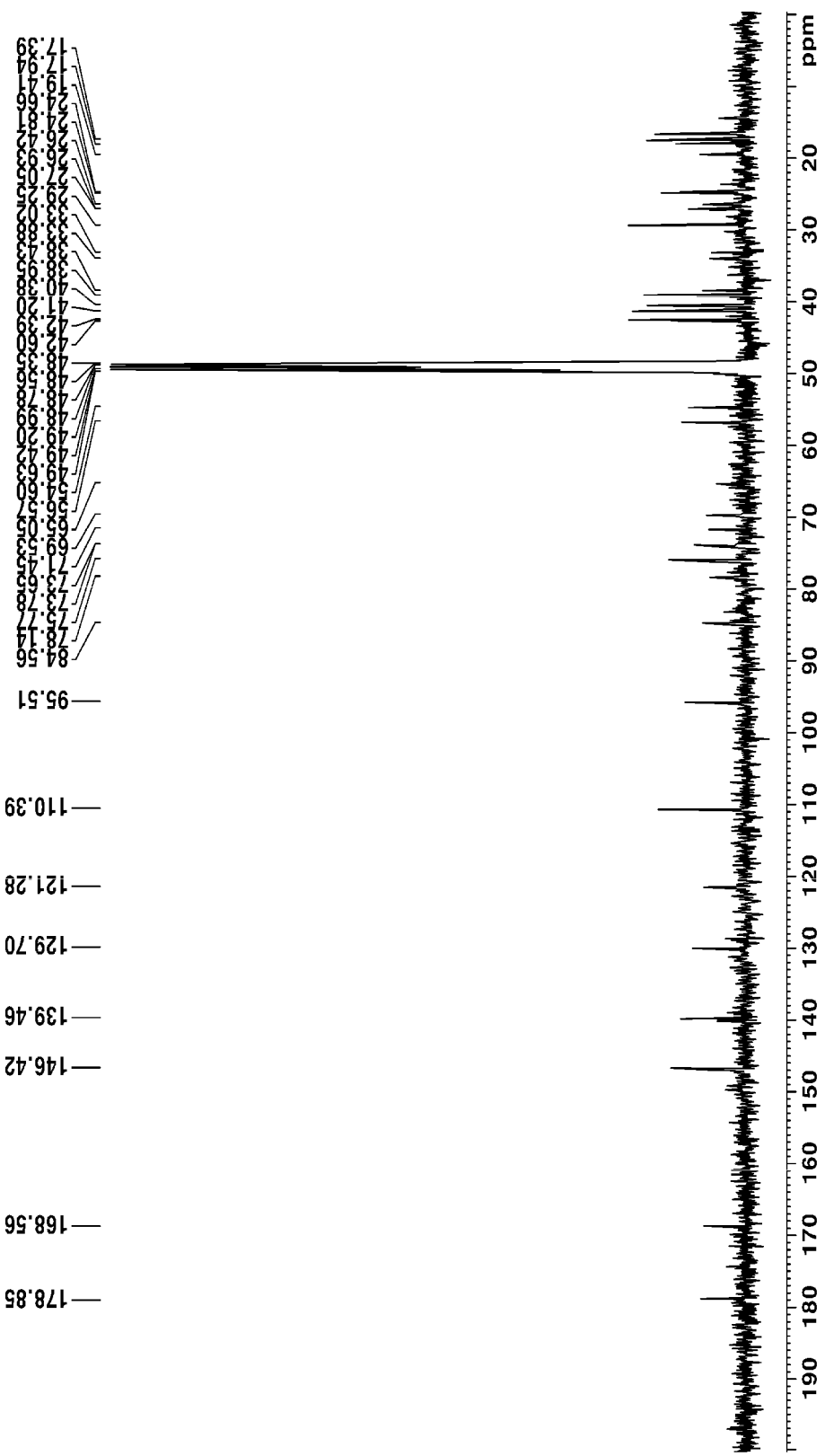
FIG. 6 is a $^{13}$C NMR of novel compound 1, purely isolated from the ethyl acetate fraction fractionated from the *Filipendula glaberrima* alcohol extract using various kinds of column chromatography.
Figure 7:
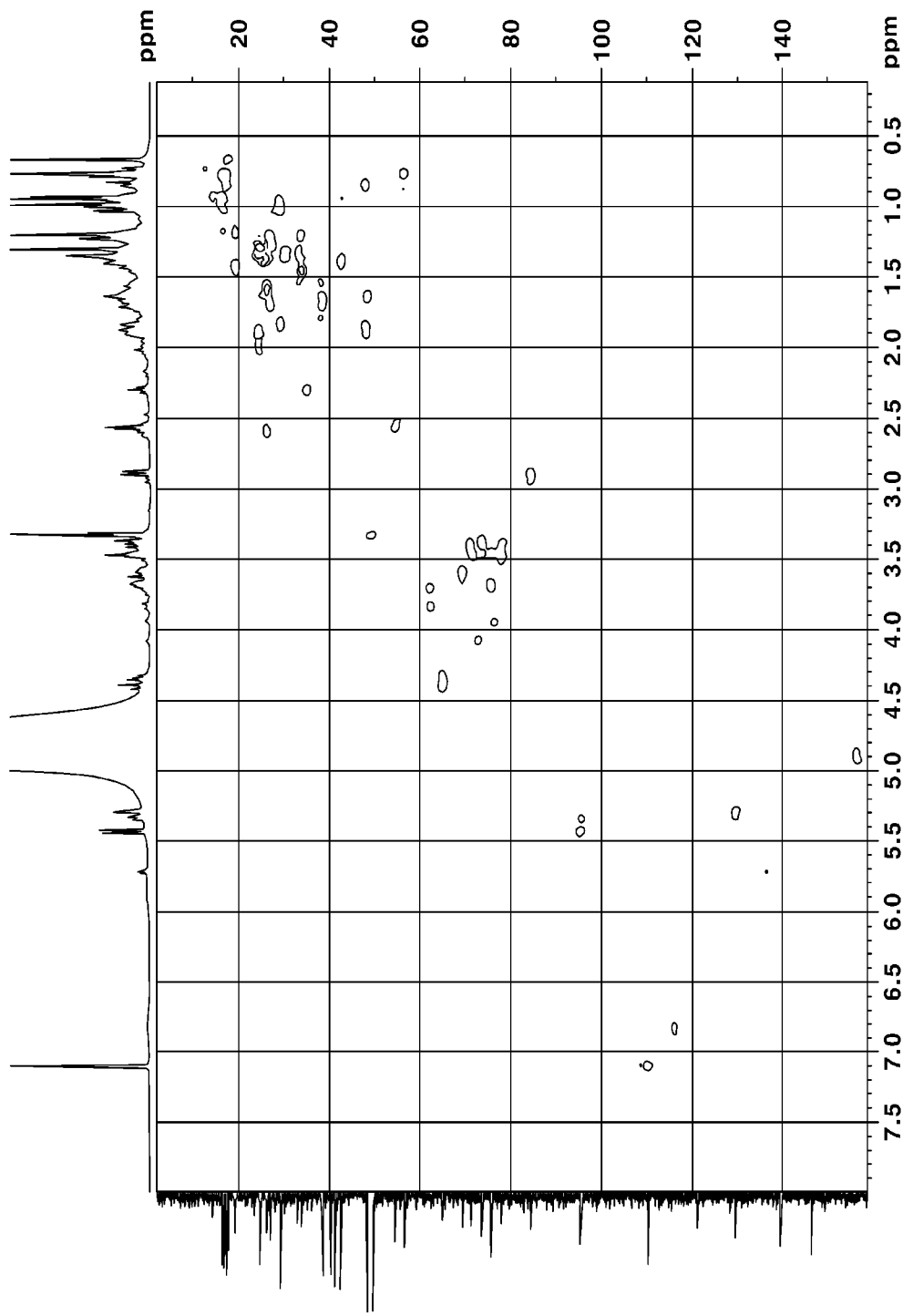
FIG. 7 is a HSQC NMR of novel compound 1, purely isolated from the ethyl acetate fraction fractionated from the *Filipendula glaberrima* alcohol extract using various kinds of column chromatography.
Figure 8:
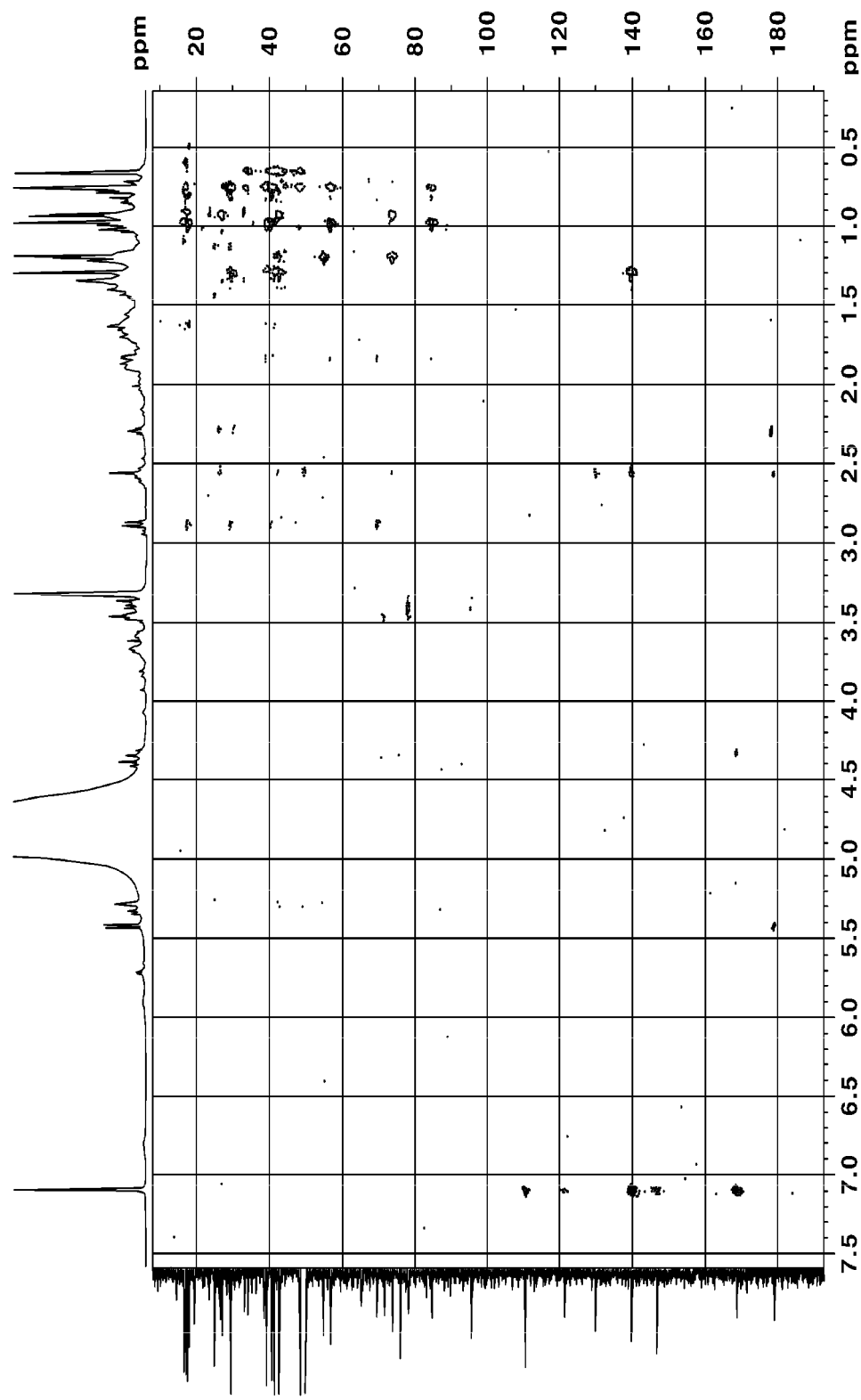
FIG. 8 is a HMBC NMR of novel compound 1, purely isolated from the ethyl acetate fraction fractionated from the *Filipendula glaberrima* alcohol extract using various kinds of column chromatography.
Figure 9:
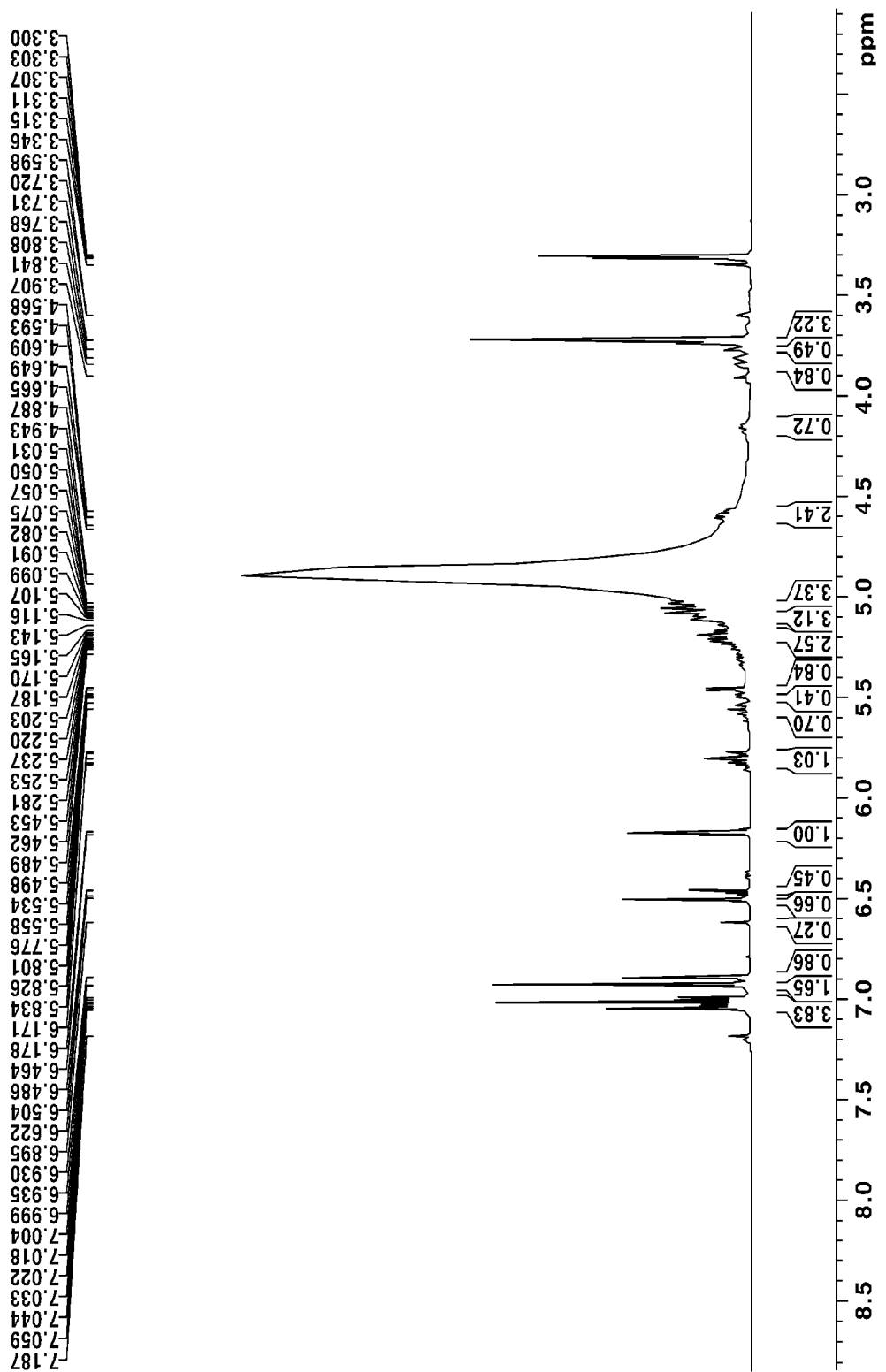
FIG. 9 is a $^1$H NMR of novel compound 2, purely isolated from the ethyl acetate fraction fractionated from the *Filipendula glaberrima* alcohol extract using various kinds of column chromatography.
Figure 10:
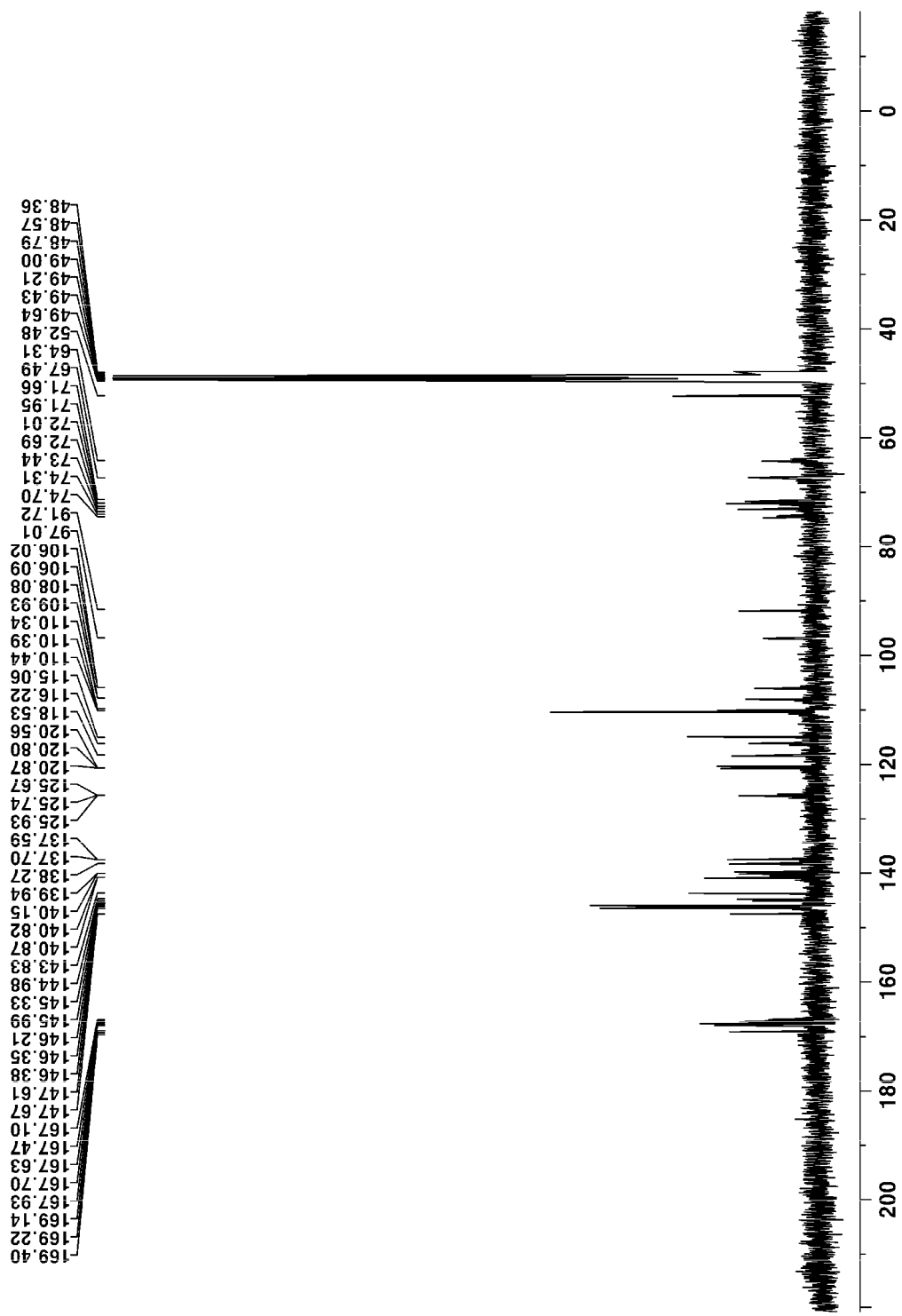
FIG. 10 is a $^{13}$C NMR of novel compound 2, purely isolated from the ethyl acetate fraction fractionated from the *Filipendula glaberrima* alcohol extract using various kinds of column chromatography.
Figure 11:
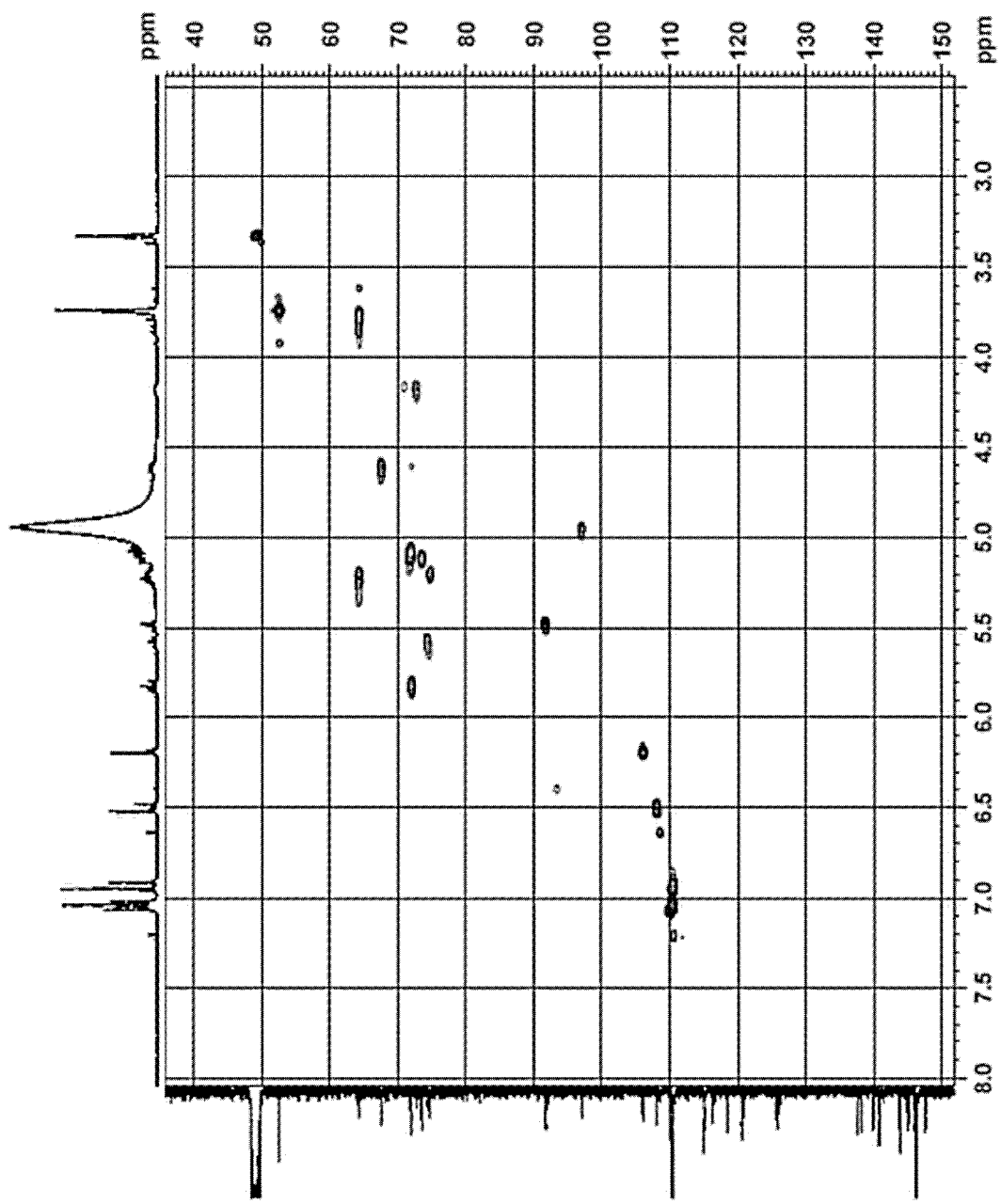
FIG. 11 is a HSQC NMR of novel compound 2, purely isolated from the ethyl acetate fraction fractionated from the *Filipendula glaberrima* alcohol extract using various kinds of column chromatography.
Figure 12:
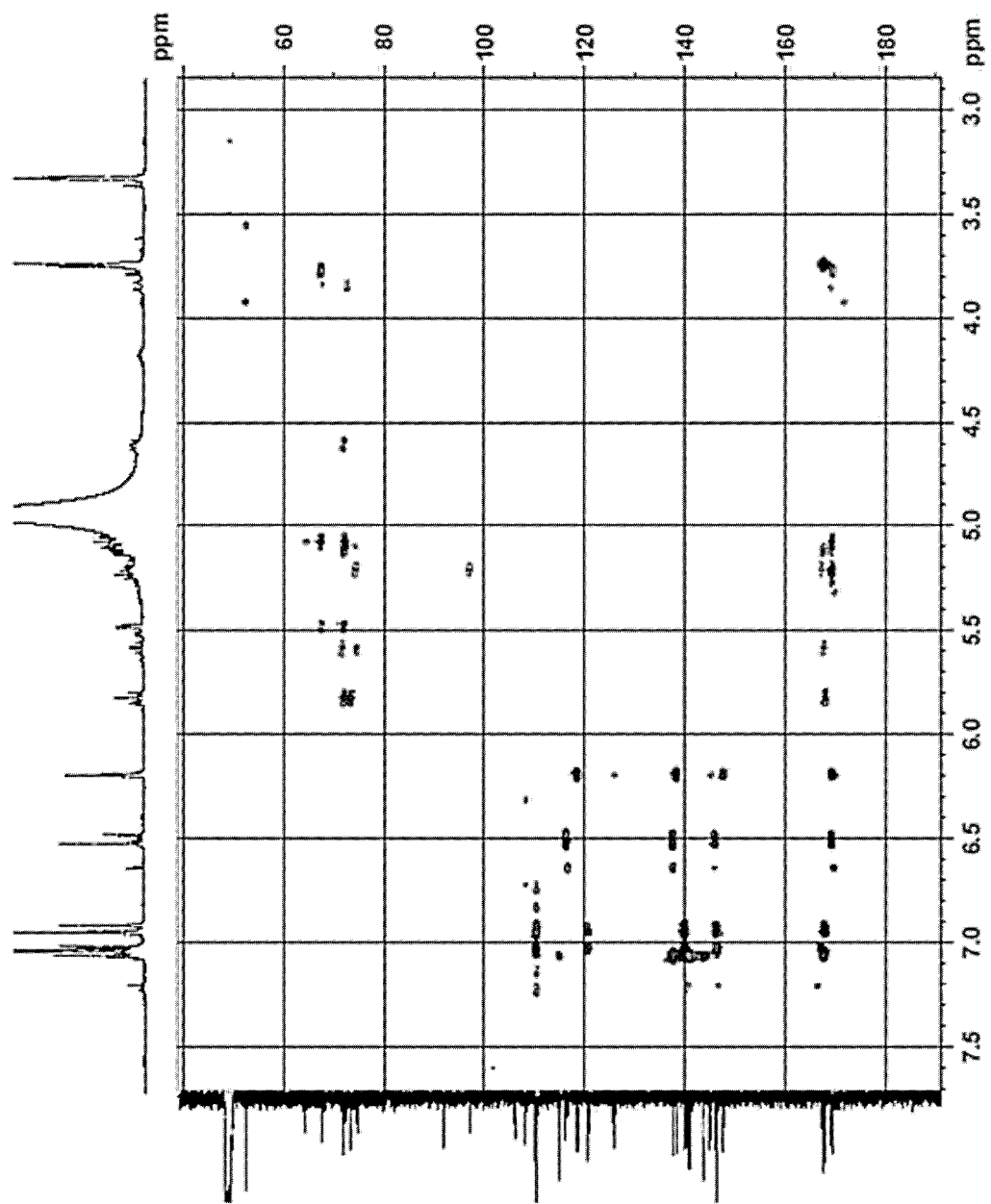
FIG. 12 is a HMBC NMR of novel compound 2, purely isolated from the ethyl acetate fraction fractionated from the *Filipendula glaberrima* alcohol extract using various kinds of column chromatography.

Experimental Example 3. Effect of Inhibiting Formation of Foam Cells in Macrophages by *Filipendula glaberrima* Extract 1) Cell Culture and Treatment Conditions The cells were human monocyte THP-1 purchased from ATCC corporation and cultured in medium conditions of high glucose DMEM+10% FBS+1% P/S, and oxidized LDL (ox-LDL) was purchased from Invitrogen. Experiments were performed through treatment with pravastatin at a concentration of 5 µM as a positive control. That is, the THP-1 cells were maintained in 1% FBS for 6 hours, treated with control and test substances and, after 2 hours, further treated with 25 µg/ml of ox-LDL. After 16 hours, the cells were fixed with 4% paraformaldehyde and subjected to Oil Red O staining, the reagent used to stain in the cells was eluted with 100% isopropanol, and absorbance was measured at a wavelength of 450 nm. The results are shown in FIGS. 3 and 4.

It is known that, in the early stage of atherosclerosis, monocytes, etc., are differentiated into macrophages by adherent molecular substances, and the macrophages internalize modified LDLs using scavenger receptors and are then transformed into foam cells, which cause lipids to be deposited in blood vessels, resulting in arteriosclerosis. As can be seen from FIGS. 3 and 4, the *Filipendula glaberrima* extracts and the solvent fractions exhibit an excellent effect of inhibiting the formation of foam cells in a concentration-dependent manner. In particular, the *Filipendula glaberrima* ethyl acetate solvent fraction (Fg-AE) and the butanol fraction (Fg-AB) exhibit a remarkably excellent effect of inhibiting the formation of foam cells, which is comparable to the effect of the reference drug pravastatin currently used in clinic, and thus have high potential to be developed as natural materials that help prevent vascular diseases such as arteriosclerosis.

As described above, each of the *Filipendula glaberrima* extracts and solvent fractions thereof according to the present invention exhibits an antioxidant effect, and remarkable effects of inhibiting HMG-CoA reductase, of inhibiting the formation of foam cells in macrophages and of lowering the concentration of cholesterol in the blood, thus being useful as active ingredients in pharmaceutical compositions or health food compositions for treating, preventing and ameliorating hypercholesterolemia, or heart diseases or vascular diseases caused by hypercholesterolemia.

Preparation Example

Meanwhile, the pharmaceutical composition containing the *Filipendula glaberrima* extract or solvent fraction thereof according to the present invention can be prepared in various forms according to the purpose thereof. The following Preparations 1 to 4 illustrate a method for preparing a drug containing, as an active ingredient, the *Filipendula glaberrima* extract or solvent fraction thereof according to the present invention, but the present invention is not limited thereto.

Preparation 1: Tablets (Direct Compression)

5.0 mg of an active ingredient was sieved and mixed with 14.1 mg of lactose, 0.8 mg of crospovidone USNF and 0.1 mg of magnesium stearate, and the mixture was compressed into tablets.

Preparation 2: Tablets (Wet Granulation)

5.0 mg of an active ingredient was sieved and was mixed with 16.0 mg of lactose and 4.0 mg of starch. 0.3 mg of Polysorbate 80 was dissolved in pure water, and an appropriate amount of the resulting solution was added to the mixture, followed by granulation. The granules were dried, sieved and mixed with 2.7 mg of colloidal silicon dioxide and 2.0 mg of magnesium stearate. The granules were compressed into tablets.

Preparation 3. Powders and Capsules 5.0 mg of an active ingredient was sieved and then mixed with 14.8 mg of lactose, 10.0 mg of polyvinylpyrrolidone and 0.2 mg of magnesium stearate. Hard No. 5 gelatin capsules were filled with the resulting mixture using an appropriate device.

Preparation 4. Injections

Injections were prepared by incorporating 100 mg of the active ingredient as well as 180 mg of mannitol, 26 mg of $Na_2HPO_4 \cdot 12H_2O$ and 2,974 mg of distilled water.

In addition, the health food composition containing the *Filipendula glaberrima* extract or solvent fraction thereof according to the present invention can be prepared in various forms according to the purpose thereof. The following Preparations 5 to 9 illustrate a method for preparing a health food containing as an active ingredient, the *Filipendula glaberrima* extract or solvent fraction thereof according to the present invention, but the present invention is not limited thereto.

Preparation 5. Granular Health Foods 1,000 mg of an active Ingredient, 70 µg of vitamin A acetate, 1.0 mg of vitamin E, 0.15 mg of vitamin $B_2$, 0.5 mg of vitamin $B_6$, 0.2 µg of vitamin $B_{12}$, 10 mg of vitamin C, 10 µg of biotin, 1.7 mg of nicotinamide, 50 µg of folic acid, 0.5 mg of calcium pantothenate, 1.75 mg of ferrous sulfate, 0.82 mg of zinc oxide, 25.3 mg of magnesium carbonate, 15 mg of potassium phosphate monobasic, 55 mg of dibasic calcium phosphate, 90 mg of potassium citrate, 100 mg of calcium carbonate, and 24.8 mg of chloride magnesium were mixed and then a granular health food was prepared according to a conventional method.

Preparation 6. Health Drink 1,000 mg of an active ingredient, 1,000 mg of citric acid, 100 g of oligosaccharide, 2 g of a plum concentrate and 1 g of taurine were mixed and purified water was added thereto to adjust the total volume to 900 ml.

After stirring and heating at 85° C. for about 1 hour, the resulting solution was filtered and charged in a sterilized 2-liter container, and the container was sealed and sterilized to prepare a health drink.

Although the composition ratio above is obtained as a mixture of components suitable for preferred drinks in a preferred example, the mixing ratio may be arbitrarily modified according to regional and ethnic preferences, such as target customers, target county and usage.

Preparation 7. Flour-Based Foods 0.5 to 5 g of an active ingredient was added to 100 g of flour, and bread, cakes, cookies, crackers and noodles were prepared using the resulting mixture to prepare foods for health improvement.

Preparation 8. Dairy Products 5 to 10 g of an active ingredient was added to 100 g of milk, and various dairy products such as butter and ice cream were prepared using the milk.

Preparation 9. Sunsik (Korean Ready-To-Eat Food Prepared From Grains)

30 g of brown rice, 20 g of barley, 10 g of glutinous rice, and 15 g of adlay were pregelatinized by a known method, dried, and roasted and then prepared into a powder having a particle size of 60 mesh with a grinder. 7 g of black beans, 7 g of black sesames seed and 7 g of perilla seeds were steamed by a known method, and then dried, roasted and then prepared into a powder having a particle size of 60 mesh with a grinder. The grains and the seeds prepared above were mixed with 3 g of the active ingredient of the present invention to prepare Sunsik.

As is apparent from the foregoing, the *Filipendula glaberrima* alcoholic extract, and the solvent fraction fractionated therefrom or novel compounds 1 and 2 purely isolated from the *Filipendula glaberrima* ethyl acetate fraction obtained through the present invention have an excellent inhibitory effect against HMG-CoA reductase activity, an excellent antioxidant effect, and a remarkably excellent effect of suppressing the formation of foam cells in macrophages. Therefore, the pharmaceutical composition or health food composition containing, as active ingredients, the *Filipendula glaberrima* alcoholic extract, and the solvent fraction fractionated therefrom or novel compounds 1 and 2 purely isolated from the *Filipendula glaberrima* ethyl acetate fraction obtained through the present invention have excellent effects of lowering blood cholesterol levels and of suppressing the formation of foam cells which are formed due to the introduction of oxidized LDL in macrophages.

The disease or disorder that can be treated, prevented or alleviated through the *Filipendula glaberrima* alcoholic extract, and the solvent fraction fractionated therefrom or novel compounds 1 and 2 purely isolated from the *Filipendula glaberrima* ethyl acetate fraction obtained through the present invention is specifically selected from the group consisting of hypercholesterolemia, hyperlipidemia, arteriosclerosis, atherosclerosis, peripheral vascular diseases, dyslipidemia, hyperbetalipoproteinemia, hypoalphalipoproteinemia, hypercholesterolemia, hypertriglyceridemia, familial hypercholesterolemia, cardiovascular disorders, coronary heart diseases, coronary artery diseases, coronary vessel diseases, angina pectoris, ischemia, cardiac ischemia, thrombosis, myocardial infarction, stroke, peripheral vascular diseases, reperfusion injury, restenosis after angioplasty, hypertension, congestive heart failure, diabetes mellitus, diabetes-related vascular complications, obesity and endotoxemia.

The effects of the present invention are not limited to those mentioned above. It should be understood that the effects of the present invention include all effects that can be inferred from the description of the present invention.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method for ameliorating or treating a cardiovascular disease of a subject, wherein the method comprises administering an effective amount of a fraction of *Filipendula glaberrima* extract to the subject in need thereof, wherein the fraction is an ethyl acetate fraction of *Filipendula glaberrima* $C_1$-$C_5$ alcohol extract.

2. The method according to claim 1, wherein the fraction of *Filipendula glaberrima* extract is an extract of an aerial or underground part of *Filipendula glaberrima*.

3. The method according to claim 1, wherein the fraction of the *Filipendula glaberrima* extract ameliorates or treats the cardiovascular disease through at least one of suppression of HMG-CoA reductase activity, suppression of foam cell production, and suppression of lipid peroxide production.

4. The method according to claim 1, wherein the fraction of the *Filipendula glaberrima* extract is administered in a form of health food composition.

5. The method according to claim 1, wherein the fraction of the *Filipendula glaberrima* extract is administered in a form of pharmaceutical composition.

6. The method according to claim 5, wherein the pharmaceutical composition is formulated in the form of any one of injections, powders, granules, tablets, capsules, suspensions, emulsions, syrups, aerosols and external preparations.

7. The method according to claim 1, wherein the cardiovascular disease comprises at least one selected from the group consisting of hypercholesterolemia, hyperlipidemia, arteriosclerosis, atherosclerosis, peripheral vascular diseases, dyslipidemia, hyperbetalipoproteinemia, hypoalphalipoproteinemia, hypercholesterolemia, hypertriglyceridemia, familial hypercholesterolemia, cardiovascular disorders, coronary heart diseases, coronary artery diseases, coronary vessel diseases, angina pectoris, ischemia, cardiac ischemia, thrombosis, myocardial infarction, stroke, peripheral vascular diseases, reperfusion injury, restenosis after angioplasty, hypertension, congestive heart failure, diabetes mellitus, diabetes-related vascular complications, obesity and endotoxemia.

* * * * *